(12) United States Patent
Sakurai et al.

(10) Patent No.: US 10,195,270 B2
(45) Date of Patent: Feb. 5, 2019

(54) PEPTIDE/β-1,3-GLUCAN COMPLEX AND PRODUCTION METHOD THEREOF AND PHARMACEUTICAL COMPOSITION CONTAINING PEPTIDE/β-1,3-GLUCAN COMPLEX

(71) Applicant: Japan Science and Technology Agency, Kawaguchi-shi, Saitama (JP)

(72) Inventors: Kazuo Sakurai, Kitakyushu (JP); Shin-ichi Mochizuki, Kitakyushu (JP); Hiromi Morishita, Kitakyushu (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 0 days.

(21) Appl. No.: 15/116,306

(22) PCT Filed: Dec. 25, 2014

(86) PCT No.: PCT/JP2014/084374
§ 371 (c)(1),
(2) Date: Aug. 3, 2016

(87) PCT Pub. No.: WO2015/118789
PCT Pub. Date: Aug. 13, 2015

(65) Prior Publication Data
US 2017/0007695 A1    Jan. 12, 2017

(30) Foreign Application Priority Data

Feb. 6, 2014   (JP) ................ 2014-021333

(51) Int. Cl.
| | | |
|---|---|---|
| *C12N 7/00* | (2006.01) |
| *A61K 47/64* | (2017.01) |
| *A61K 39/39* | (2006.01) |
| *A61K 39/29* | (2006.01) |
| *A61K 39/15* | (2006.01) |
| *A61K 39/13* | (2006.01) |
| *A61K 39/00* | (2006.01) |
| *A61K 39/385* | (2006.01) |
| *A61K 31/7088* | (2006.01) |
| *C07K 14/77* | (2006.01) |
| *C07K 19/00* | (2006.01) |
| *A61K 39/015* | (2006.01) |
| *A61K 39/145* | (2006.01) |
| *A61K 39/205* | (2006.01) |

(Continued)

(52) U.S. Cl.
CPC ........ *A61K 39/385* (2013.01); *A61K 31/7088* (2013.01); *A61K 39/0011* (2013.01); *A61K 39/015* (2013.01); *A61K 39/13* (2013.01); *A61K 39/145* (2013.01); *A61K 39/15* (2013.01); *A61K 39/205* (2013.01); *A61K 39/245* (2013.01); *A61K 39/292* (2013.01); *A61K 39/39* (2013.01); *A61K 47/646* (2017.08); *C07K 14/77* (2013.01); *C07K 19/00* (2013.01); *C12N 7/00* (2013.01); *C12N 15/117* (2013.01); *A61K 2039/55561* (2013.01); *A61K 2039/55566* (2013.01); *A61K 2039/572* (2013.01); *A61K 2039/6025* (2013.01); *A61K 2039/6081* (2013.01); *A61K 2039/6087* (2013.01); *C12N 2310/17* (2013.01); *C12N 2320/31* (2013.01); *C12N 2710/16634* (2013.01); *C12N 2730/10134* (2013.01); *C12N 2740/16034* (2013.01); *C12N 2760/16134* (2013.01); *C12N 2760/18034* (2013.01); *C12N 2770/32634* (2013.01)

(58) Field of Classification Search
None
See application file for complete search history.

(56) References Cited

U.S. PATENT DOCUMENTS

| | | | | |
|---|---|---|---|---|
| 7,790,189 B2 * | 9/2010 | Mizu | ............. | A61K 9/0019 424/278.1 |
| 8,076,294 B2 * | 12/2011 | Kinney | ............. | A61K 38/39 514/17.2 |
| 9,713,636 B2 * | 7/2017 | Rii | ............. | C12N 15/113 |

(Continued)

FOREIGN PATENT DOCUMENTS

| | | | |
|---|---|---|---|
| JP | 2000-273182 A | 10/2000 |
| JP | 2001-503254 A | 3/2001 |

(Continued)

OTHER PUBLICATIONS

Anada et al, Linear double-stranded DNA that mimics an infective tail of virus genome to enhance transfection, Journal of Controlled Release, 2005, 108:529-539 (Year: 2005).*

Matsumoto et al, Chemically modified polysaccharide schizophyllan for antisense oligonucleotides delivery to enhance the cellular uptake efficiency, BBA, 2004, 1670:91-104 (Year: 2004).*

(Continued)

*Primary Examiner* — Nita M. Minnifield

(57) ABSTRACT

This peptide/β-1,3-glucan complex includes β-1,3-glucan and a peptide/polynucleotide conjugate in which an antigenic peptide is bonded covalently to a polynucleotide or a derivative thereof. The polynucleotide or derivative thereof of the peptide/polynucleotide conjugate bonds via a hydrogen bond with β-1,3-glucan, forming a complex having a triple helix structure including a single molecular chain of the polynucleotide or derivative thereof and two molecular chains of the β-1,3-glucan. Alternatively, the side chain of the β-1,3-glucan and the antigenic peptide are bonded covalently formed by either a cycloaddition reaction between an alkyne and an azide derivative, or a reaction between a maleimide group or a vinyl sulfone group and a thiol group.

16 Claims, 6 Drawing Sheets
Specification includes a Sequence Listing.

(51) Int. Cl.
    A61K 39/245        (2006.01)
    C12N 15/117        (2010.01)

(56)            References Cited

U.S. PATENT DOCUMENTS

| | | | |
|---|---|---|---|
| 9,943,607 B2* | 4/2018 | Bose | A61K 39/39 |
| 2005/0214256 A1 | 9/2005 | Megede et al. | |
| 2007/0166820 A1 | 7/2007 | Smith et al. | |
| 2008/0262210 A1* | 10/2008 | Mizu | A61K 9/0019 |
| | | | 536/23.1 |
| 2009/0068246 A1* | 3/2009 | Kinney | A61K 38/39 |
| | | | 424/423 |
| 2013/0142832 A1* | 6/2013 | Sakurai | C12N 15/113 |
| | | | 424/278.1 |
| 2013/0267576 A1* | 10/2013 | Sakurai | C07H 21/04 |
| | | | 514/44 A |
| 2014/0128448 A1* | 5/2014 | Rii | C12N 15/113 |
| | | | 514/44 A |
| 2015/0148529 A1* | 5/2015 | Sakurai | A61K 31/711 |
| | | | 536/24.5 |
| 2016/0208260 A1* | 7/2016 | Ishii | A61K 39/145 |
| 2017/0007695 A1* | 1/2017 | Sakurai | C07K 14/77 |
| 2018/0256738 A1* | 9/2018 | Bose | A61K 39/39 |

FOREIGN PATENT DOCUMENTS

| | | |
|---|---|---|
| JP | 2007-070307 A | 3/2007 |
| JP | 2010-174107 A | 8/2010 |
| JP | 2012-050450 A | 3/2012 |
| JP | 2013-146270 A | 8/2013 |
| JP | 2013-147464 A | 8/2013 |
| TW | 201400496 A | 1/2014 |
| WO | 96/14873 A2 | 5/1996 |
| WO | 01/34207 A1 | 5/2001 |
| WO | 02/072152 A1 | 9/2002 |
| WO | WO-2015041318 A1 * | 3/2015 ........... A61K 39/145 |
| WO | WO-2015118789 A1 * | 8/2015 ............ C07K 14/77 |
| WO | WO-2016098832 A1 * | 6/2016 ............ A61K 47/36 |

OTHER PUBLICATIONS

Anada et al, Proposal of new modification technique for linear double-stranded DNAs using the polysaccharide schizopyllan, Bioorganic and Medicinal Chemistry Letters, 2004, 14:5655-5659 (Year: 2004).*

Anada et al, Transferrin-appended β-(1-→3)-D-glucan schizophyllan for antisense oligonucleotides delivery to enhance the cellular uptake, e-Journal of Surface Science and Nanotechnology, Jun. 10, 2005, 3:195-202 (Year: 2005).*

The International Bureau of WIPO, "Notification of Transmittal of Translation of the International Preliminary Report on Patentability," issued in International Application No. PCT/JP2014/084374 of which U.S. Appl. No. 15/116,306 is a U.S. national phase entry, dated Aug. 18, 2016, 11 pages.

M.G. Finn et al., "Click Chemistry no Gainen to Oyo: Teishosha no Tachiba kara", Chemistry & chemical industry, vol. 60, No. 10, pp. 976-980 (Oct. 2007).

Christopher D. Hein et al., "Click Chemistry, A Powerful Tool for Pharmaceutical Sciences", Pharmaceutical Research, vol. 25, No. 10, pp. 2216-2230 (Oct. 2008).

Arthur M. Krieg, "CpG Motifs in Bacterial DNA and Their Immune Effects", Annual Review of Immunology, vol. 20, pp. 709-760 (2002).

Yoshiya Maegawa et al., "Specific Delivery of Peptide to Antigen Presenting Cells Using Beta-(1,3)-D-Glucan", The 41st International Symposium on Nucleic Acids Chemistry 2014, Program & Abstracts, pp. 390-391, Nov. 17, 2014 (date of receipt).

Kentaro Miyoshi et al., "Polysaccharide-Polynucleotide Complexes. Part 32. Structural Analysis of the Curdlan/Poly (cytidylic acid) Complex with Semiempirical Molecular Orbital Calculations", Biomacromolecules, vol. 6, pp. 1540-1546 (2005).

Masami Mizu et al., "A Polysaccharide Carrier for Immunostimulatory CpG DNAs to Enhance Cytokine Secretion", Journal of the American Chemical Society, Communications, vol. 126, pp. 8372-8373 (2004).

Masami Mizu et al., "Protection of polynucleotides against nuclease-mediated hydrolysis by complexation with schizophyllan", Biomaterials, vol. 25, Issue 15, pp. 3109-3116 (2004).

Shinichi Mochizuki and Kazuo Sakurai, "Dectin-1 targeting delivery of TNF-α antisense ODNs complexed with β-1,3-glucan protects mice from LPS-induced hepatitis", Journal of Controlled Release, vol. 151, pp. 155-161 (2011).

Shinichi Mochizuki et al., "Application of peptide/CpG-DNA/β-1, 3-glucan complex for novel cancer vaccine", Polymer Preprints, Japan, vol. 63, No. 2, pp. 7408-7409 (Sep. 3, 2014).

N. Mohagheghpour et al., "Glucans as Immunological Adjuvants" Immunobiology of Proteins and Peptides VIII (Advances in Experimental Medicine and Biology), vol. 383, pp. 13-22 (1995).

Kazuo Sakurai and Seiji Shinkai, "Molecular Recognition of Adenine, Cytosine, and Uracil in a Single-Stranded RNA by a Natural Polysaccharide: Schizophyllan", Journal of the American Chemical Society, vol. 122, pp. 4520-4521 (2000).

Kazuo Sakurai et al., "Polysaccharide-Polynucleotide Complexes. 2. Complementary Polynucleotide Mimic Behavior of the Natural Polysaccharide Schizophyllan in the Macromolecular Complex with Single-Stranded RNA and DNA", Biomacromolecules, vol. 2, pp. 641-650 (2001).

Naohiko Shimada et al., "Synthesis and in Vitro Characterization of Antigen-Conjugated Polysaccharide as a CpG DNA Carrier", Bioconjugate Chemistry, vol. 17, pp. 1136-1140 (2006).

"5. Microbial DNA (CpG DNA) and TLR9", Standard Immunotherapy, 2nd Edition, Ed. Masaru Taniguchi and Masayuki Miyasaka, Igaku-Shoin, p. 333 (2002), Print.

Taiwan Patent Office, "Office Action", issued in Taiwanese Patent Application No. 103146265, dated Sep. 21, 2015, 9 pages (3 pages of English translation of Office Action, and 6 pages of Office Action).

Robert Vaughan et al., "Mapping protein—RNA interactions", Virus Adaptation and Treatment, vol. 4, pp. 29-41 (2012).

Hermann Wagner, "Bacterial CpG DNA Activates Immune Cells to Signal Infectious Danger", Advances in Immunology, vol. 73, pp. 329-368 (1999).

Saburo Yamamoto et al., "The discovery of immunostimulatory DNA sequence", Springer Semin Immunopathol, vol. 22, pp. 11-19 (2000).

Xu Zhang et al., "In situ self-assembly of peptides in glucan particles for macrophage-targeted oral delivery", Journal of Materials Chemistry B, vol. 2, pp. 5882-5890 (Sep. 9, 2014).

Hidetoshi Takedatsu et al., "A New Therapeutic Approach Using a Schizophyllan-based Drug Delivery System for Inflammatory Bowel Disease," Molecular Therapy, vol. 20, No. 6, pp. 1234-1241, Jun. 2012, The American Society of Gene & Cell Therapy.

European Patent Office, "Office Action," issued in European Patent Application No. 14 881 734.9, which is a European counterpart of U.S. Appl. No. 15/116,306, dated Dec. 22, 2017, 8 pages.

Japan Patent Office, "Office Action," issued in Japanese Patent Application No. 2015-561185, which is a Japanese counterpart of U.S. Appl. No. 15/116,306, dated Feb. 20, 2018, 7 pages (4 pages of English translation of Office Action and 3 pages of Office Action).

* cited by examiner dA40(S)(alkyne)　　　　OVA(N3)　　　　OVA peptide -dA40(S)

1 peptide-dA40S
2 CpG-dA40S
3 complex (peptide/CpG/SPG)

SEQUENCE LISTING

```
<160> NUMBER OF SEQ ID NOS: 28

<210> SEQ ID NO 1
<211> LENGTH: 8
<212> TYPE: PRT
<213> ORGANISM: Homo sapiens

<400> SEQUENCE: 1

Ser Ile Ile Asn Phe Glu Lys Leu
1               5

<210> SEQ ID NO 2
<211> LENGTH: 20
<212> TYPE: DNA
<213> ORGANISM: Artificial Sequence
<220> FEATURE:
<223> OTHER INFORMATION: nonmethylated CpG sequence for ajuvant

<400> SEQUENCE: 2
atcgactctc gagcgttctc                                                     20

<210> SEQ ID NO 3
<211> LENGTH: 9
<212> TYPE: PRT
<213> ORGANISM: Mus musculus

<400> SEQUENCE: 3
```

```
Glu Gly Ser Arg Asn Gln Asp Trp Leu
1               5

<210> SEQ ID NO 4
<211> LENGTH: 9
<212> TYPE: PRT
<213> ORGANISM: Homo sapiens

<400> SEQUENCE: 4

Lys Val Pro Arg Asn Gln Asp Trp Leu
1               5

<210> SEQ ID NO 5
<211> LENGTH: 9
<212> TYPE: PRT
<213> ORGANISM: Homo sapiens

<400> SEQUENCE: 5

Ser Pro Ser Tyr Val Tyr His Gln Phe
1               5

<210> SEQ ID NO 6
<211> LENGTH: 9
<212> TYPE: PRT
<213> ORGANISM: Influenza A virus

<400> SEQUENCE: 6

Ile Tyr Ser Thr Val Ala Ser Ser Leu
1               5

<210> SEQ ID NO 7
<211> LENGTH: 9
<212> TYPE: PRT
<213> ORGANISM: Influenza A virus

<400> SEQUENCE: 7

Ala Ser Asn Glu Asn Met Asp Thr Met
1               5

<210> SEQ ID NO 8
<211> LENGTH: 10
<212> TYPE: PRT
<213> ORGANISM: Influenza A virus

<400> SEQUENCE: 8

Ser Ser Leu Glu Asn Phe Arg Ala Tyr Val
1               5                   10

<210> SEQ ID NO 9
<211> LENGTH: 8
<212> TYPE: PRT
<213> ORGANISM: Homo sapiens

<400> SEQUENCE: 9

Asp Ala Pro Ile Tyr Thr Asn Val
1               5

<210> SEQ ID NO 10
<211> LENGTH: 8
<212> TYPE: PRT
<213> ORGANISM: Mouse leukemogenic retrovirus

<400> SEQUENCE: 10

Lys Ser Pro Trp Phe Thr Thr Leu
```

```
<210> SEQ ID NO 11
<211> LENGTH: 9
<212> TYPE: PRT
<213> ORGANISM: Sendai virus

<400> SEQUENCE: 11

Phe Ala Pro Gly Asn Tyr Pro Ala Leu
1               5

<210> SEQ ID NO 12
<211> LENGTH: 9
<212> TYPE: PRT
<213> ORGANISM: Mouse cytomegalovirus 1

<400> SEQUENCE: 12

Tyr Pro His Phe Met Pro Thr Asn Leu
1               5

<210> SEQ ID NO 13
<211> LENGTH: 9
<212> TYPE: PRT
<213> ORGANISM: Lymphocytic choriomeningitis virus

<400> SEQUENCE: 13

Lys Ala Val Tyr Asn Phe Ala Thr Met
1               5

<210> SEQ ID NO 14
<211> LENGTH: 9
<212> TYPE: PRT
<213> ORGANISM: Lymphocytic choriomeningitis virus

<400> SEQUENCE: 14

Phe Gln Pro Gln Asn Gly Gln Phe Ile
1               5

<210> SEQ ID NO 15
<211> LENGTH: 9
<212> TYPE: PRT
<213> ORGANISM: Lymphocytic choriomeningitis virus

<400> SEQUENCE: 15

Arg Pro Gln Ala Ser Gly Val Tyr Met
1               5

<210> SEQ ID NO 16
<211> LENGTH: 9
<212> TYPE: PRT
<213> ORGANISM: Plasmodium malariae

<400> SEQUENCE: 16

Ser Tyr Ile Pro Ser Ala Glu Lys Ile
1               5

<210> SEQ ID NO 17
<211> LENGTH: 10
<212> TYPE: PRT
<213> ORGANISM: Human immunodeficiency virus

<400> SEQUENCE: 17

Arg Gly Pro Gly Arg Ala Phe Val Thr Ile
1               5                   10
```

<210> SEQ ID NO 18
<211> LENGTH: 9
<212> TYPE: PRT
<213> ORGANISM: Mycobacterium bovis

<400> SEQUENCE: 18

Gly Gly Pro His Ala Val Tyr Leu Leu
1               5

<210> SEQ ID NO 19
<211> LENGTH: 8
<212> TYPE: PRT
<213> ORGANISM: Homo sapiens

<400> SEQUENCE: 19

Glu Ala Gln Asn Thr Thr Tyr Leu
1               5

<210> SEQ ID NO 20
<211> LENGTH: 9
<212> TYPE: PRT
<213> ORGANISM: Mus musculus

<400> SEQUENCE: 20

Leu Pro Tyr Leu Gly Trp Leu Val Phe
1               5

<210> SEQ ID NO 21
<211> LENGTH: 12
<212> TYPE: PRT
<213> ORGANISM: Hepatitis B virus

<400> SEQUENCE: 21

Ile Pro Gln Ser Leu Asp Ser Trp Trp Thr Ser Leu
1               5                   10

<210> SEQ ID NO 22
<211> LENGTH: 8
<212> TYPE: PRT
<213> ORGANISM: herpes simplex virus 1

<400> SEQUENCE: 22

Ser Ser Ile Glu Phe Ala Arg Leu
1               5

<210> SEQ ID NO 23
<211> LENGTH: 9
<212> TYPE: PRT
<213> ORGANISM: Homo sapiens

<400> SEQUENCE: 23

Trp Met His His Asn Met Asp Leu Ile
1               5

<210> SEQ ID NO 24
<211> LENGTH: 9
<212> TYPE: PRT
<213> ORGANISM: artificial
<220> FEATURE:
<223> OTHER INFORMATION: an epitope derived from enhanced green
      fluorescent protein

<400> SEQUENCE: 24

His Tyr Leu Ser Thr Gln Ser Ala Leu
1               5

```
<210> SEQ ID NO 25
<211> LENGTH: 9
<212> TYPE: PRT
<213> ORGANISM: Homo sapiens

<400> SEQUENCE: 25

Thr Tyr Leu Pro Thr Asn Ala Ser Leu
1               5

<210> SEQ ID NO 26
<211> LENGTH: 8
<212> TYPE: PRT
<213> ORGANISM: Vesicular stomatitis virus

<400> SEQUENCE: 26

Arg Gly Tyr Val Tyr Gln Gly Leu
1               5

<210> SEQ ID NO 27
<211> LENGTH: 9
<212> TYPE: PRT
<213> ORGANISM: Polyomavirus

<400> SEQUENCE: 27

Arg Arg Leu Gly Arg Thr Leu Leu Leu
1               5

<210> SEQ ID NO 28
<211> LENGTH: 8
<212> TYPE: PRT
<213> ORGANISM: Artificial Sequence
<220> FEATURE:
<223> OTHER INFORMATION: random sequence of SEQ:ID No. 1

<400> SEQUENCE: 28

Phe Lys Ile Leu Ser Glu Asn Ile
1               5
```

PEPTIDE/β-1,3-GLUCAN COMPLEX AND PRODUCTION METHOD THEREOF AND PHARMACEUTICAL COMPOSITION CONTAINING PEPTIDE/β-1,3-GLUCAN COMPLEX

CROSS REFERENCE TO RELATED APPLICATIONS

This patent application is a U.S. national stage application under 35 U.S.C. § 371 of International Patent Application No. PCT/JP2014/084374 filed on Dec. 25, 2014, which claims the benefit of foreign priority to Japanese Patent Application No. JP 2014-021333 filed on Feb. 6, 2014. The International Application was published in Japanese on Aug. 13, 2015, as International Publication No. WO 2015/118789 A1 under PCT Article 21(2).

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The sequence listings disclosed in the ASCII text file submitted herewith, named "seqlist.txt" and created on Jul. 19, 2016, the size of which is 4,927 bytes, are hereby incorporated by reference.

TECHNICAL FIELD

The present disclosure relates to a novel peptide/β-1,3-glucan complex, a production method thereof and a pharmaceutical composition including the peptide/β-1,3-glucan complex.

BACKGROUND ART

The basic principle of infection prevention by vaccine is based on artificial pseudo-infection to induce acquired immunity, and to induce cellular immunity and antibody production against a specific pathogen. In acquired immunity, T cells and B cells in charge of immune "memory" play a central role, and variability of the variable region of the antibodies due to recombination of DNA is known to make possible an immune response having specificity for numerous antigens. On the other hand, in innate immunity, in which phagocytic cells such as leucocytes, macrophages, dendritic cells and the like play a central role is previously thought to perform non-specific phagocytic processing of pathogen and foreign objects, and to act only as a "temporary fix" until the establishment of acquired immunity. However, advances in research relating to the molecular mechanism of innate immunity reveals that specific recognition of self-versus-non-self clearly occurs, and innate immunity is indispensable for the establishment of acquired immunity. More specifically, recent research makes clear that the Toll-like receptor (TLR) family present in antigen-presenting cells, such as dendritic cells, macrophages, B cells and the like, induces acquired immunity through a reaction with various types of pathogens, induction of the production of cytokine, promotion of the differentiation of naïve T cells into Th1 cells, activation of killer T cells and the like.

One of a wide range of constituent components of pathogens recognized by a series of TLR family is a DNA having a CpG sequence (CpG DNA), which is a TLR9 ligand. The CpG sequence is a sequence of six bases having cysteine (C) and guanine (G) adjacent to one another at the central part of the sequence, and this base sequence is seldom found in mammals, although often seen in microorganisms. Moreover, most of the infrequently occurring CpG sequences in mammals are methylated. The non-methylated CpG sequences, which hardly exist in mammals, have strong immunostimulatory activity (for example, see Non-Patent Literature 1 to 3). CpG DNA imported into the cell by endocytosis is recognized by TLR9 present in the phagosome-like endoplasmic reticulum and strongly induces the Th1 reaction. In addition to suppressing the allergic reaction dominated by the Th2 reaction, the Th1 reaction has strong anti-tumorigenic activity. Thus in addition to protecting against infection, CpG DNA is anticipated to act as an adjuvant with respect to allergies and neoplastic disorders (for example, see Non-Patent Literature 4).

However, attempting to use CpG DNA as an immune therapy adjuvant leads to the problem of how to get the CpG DNA to arrive within the target cell while avoiding decomposition by nucleases in the cytoplasm and blood plasma and non-specific bonding with proteins.

The present inventors have paid attention to a polysaccharide having a β-1,3-glucan backbone (abbreviated hereinafter as "β-1,3-glucan") as a novel gene carrier and discovered that β-1,3-glucan forms a new type of complex with various nucleic acids including nucleic acid medicines (anti-sense DNA, CpG DNA) (for example, see Patent Literature 1 and 2, and Non-Patent Literature 5-7).

The formation of a triple-strand helix complex by two β-1,3-glucan molecules and a single nucleic acid molecule is found to take place after dissolving β-1,3-glucan, which adopts a triple-strand helix structure in nature, in an aprotic polar organic solvent such as dimethyl sulfoxide (DMSO) and the like or in a 0.1N or stronger alkaline solution, to cause disassociation of the triple-strand helix into a single strand, adding a single-stranded nucleic acid, and switching the solvent to water or bringing the pH of the alkaline solution to neutral. In this case, β-1,3-glucan molecules and the nucleic acid molecule in the triple-strand helix complex are considered to form intermolecular bonding mainly through hydrogen bonds and hydrophobic interaction.

By complexation of the nucleic acid and β-1,3-glucan in the above described manner, the nucleic acid may be delivered into the cell while suppressing hydrolysis of the nucleic acid molecule by nucleases in the cytoplasm, and while suppressing undesirable interactions between the nucleic acid molecule and proteins in the body such as non-specific bonding of the nucleic acid molecules with proteins in the blood plasma. CpG DNA is successfully delivered into the cell by using the complex of β-1,3-glucan and nucleic acid, and by using a ternary complex further containing an antigenic peptide, as seen, for example, in Patent Literature 3 and 4, and in Non-Patent Literature 9 to 11.

CITATION LIST

Patent Literature

Patent Literature 1: International Publication No. WO01/34207
Patent Literature 2: International Publication No. WO02/072152
Patent Literature 3: Unexamined Japanese Patent Application Kokai Publication No. 2010-174107

Patent Literature 4: Unexamined Japanese Patent Application Kokai Publication No. 2007-70307

Non-Patent Literature

Non-Patent Literature 1: Bacterial CpG DNA Activates Immune Cells to Signal Infectious Danger, H. Wagner, Adv. Immunol., 73, 329-368 (1999)
Non-Patent Literature 2: CpG Motifs in Bacterial DNA and Their Immune Effects, M. Krieg, Annu. Rev. Immunol., 20, 709-760 (2002)
Non-Patent Literature 3: The discovery of immunostimulatory DNA sequence, S. Yamamoto, T. Yamamoto, and T. Tokunaga, Springer Seminars in Immunopathology, 22, 11-19 (2000)
Non-Patent Literature 4: "Standard Immunotherapy", 2nd edition, Igaku-Shoin Ltd., 2002, p. 333
Non-Patent Literature 5: Molecular Recognition of Adenine, Cytosine, and Uracil in a Single-Stranded RNA by a Natural Polysaccharide: Schizophyllan. K. Sakurai and S. Shinkai, J. Am. Chem. Soc., 122, 4520-4521 (2000)
Non-Patent Literature 6: Polysaccharide-Polynucleotide Complexes. 2. Complementary Polynucleotide Mimic Behavior of the Natural Polysaccharide Schizophyllan in the Macromolecular Complex with Single-Stranded RNA and DNA. K. Sakurai, M. Mizu and S. Shinkai, Biomacromolecules, 2, 641-650 (2001)
Non-Patent Literature 7: Dectin-1 targeting delivery of TNF-α antisense ODNs complexed with β-1,3-glucan protects mice from LPS-induced hepatitis. S. Mochizuki and K. Sakurai, J. Control. Release, 151 (2011) 155-161
Non-Patent Literature 8: Structural Analysis of the Curdlan/Poly (cytidylic acid) Complex with Semiempirical Molecular Orbital Calculations. K. Miyoshi, K. Uezu, K. Sakurai and S. Shinkai, Biomacromolecules, 6, 1540-1546 (2005)
Non-Patent Literature 9: A Polysaccharide Carrier for Immunostimulatory CpG DNAs to Enhance Cytokine Secretion, M. Mizu, K. Koumoto, T. Anada, T. Matsumoto, M. Numata, S. Shinkai, T. Nagasaki and K. Sakurai, J. Am. Chem. Soc., 126, 8372-8373 (2004)
Non-Patent Literature 10: Protection of Polynucleotides against Nuclease-mediated Hydrolysis by Complexation with Schizophyllan, M. Mizu, K. Koumoto, T. Kimura, K. Sakurai and S. Shinkai, Biomaterials, 25, 15, 3109-3116 (2004)
Non-Patent Literature 11: Synthesis and in Vitro Characterization of Antigen-Conjugated Polysaccharide as a CpG DNA Carrier, N. Shimada, K. J. Ishii, Y. Takeda, C. Coban, Y. Torii, S. Shinkai, S. Akira and K. Sakurai, Bioconjugate Chem., 17, 1136-1140 (2006)

SUMMARY OF INVENTION

Technical Problem

However, the above-described background technology has the below-described problems. For example, in the method for production of the ternary complex of β-1,3-glucan/antigenic peptide/CpG DNA described in Non-Patent Literature 11, a conjugate in which β-1,3-glucan and a peptide having antigenicity are covalently bonded is formed by forming a formyl group on the glucose residue of the side chain of the β-1,3-glucan by periodate oxidation, followed by reacting the formyl group with an amino group of a peptide having antigenicity (abbreviated hereinafter as "antigenic paptide") by reductive amination, which has a problem of low yield. In consideration of these circumstances, for example, in the method of production of the ternary complex of β-1,3-glucan/antigenic peptide/CpG DNA described in Patent Literature 4, yield and reactivity between the amino group of the antigenic peptide and the formyl group of the side chain of the β-1,3-glucan are improved by performing the reaction of the antigenic peptide and the β-1,3-glucan having the formyl group on the side chain in alkaline aqueous solution and neutralization simultaneously, or by performing neutralization consecutively after reaction in an alkaline aqueous solution. However, control of the reaction site is difficult because of the presence of multiple amino groups in the peptide. Thus problems can occur such as differences in immunogenicity according to the reaction site of the antigenic peptide, difficulty of separation and purification as a result of the complex mixture of reaction products with β-1,3-glucan, and the like. Moreover, formation of the complex based on formation of covalent bonds between the β-1,3-glucan and antigenic peptide is cumbersome in comparison to forming the complex between β-1,3-glucan and DNA based on the formation of hydrogen bonding. Under these circumstances, problems of productivity and the like remain for the method that produces the ternary complex of β-1,3-glucan/antigenic peptide/CpG DNA as described in Patent Literature 4.

In consideration of the aforementioned circumstances, the object of the present disclosure is to provide a peptide/β-1,3-glucan complex, a production method thereof, and a pharmaceutical composition that includes the peptide/β-1,3-glucan complex, in which productivity is excellent and the peptide/β-1,3-glucan complex has high immunostimulatory activity.

Solution to Problem

In first aspect of the present disclosure according to the above-described object, the aforementioned problem is solved by providing a peptide/β-1,3-glucan complex that includes: a polysaccharide having a β-1,3-glucan backbone, and an antigenic peptide chemically bonded to the polysaccharide having the β-1,3-glucan backbone.

In the present disclosure, the expression "chemically bonded", in addition to meaning "covalent bonded" and "coordination bonded" to form intramolecular bonding, includes the meanings "ionic bonded", "hydrogen bonded" and "van der Waals bonded" to form a molecular group or atomic group.

In the peptide/β-1,3-glucan complex of the first aspect of the present disclosure, the polysaccharide having the β-1,3-glucan backbone is preferably schizophyllan, lentinan, scleroglucan, or curdlan.

In an second aspect of the present disclosure, the above-described problem is solved by providing a peptide/β-1,3-glucan complex, including:
a polysaccharide having a β-1,3-glucan backbone; and
a peptide/polynucleotide conjugate in which an antigenic peptide is bonded covalently to a polynucleotide or derivative thereof, wherein
the polynucleotide or derivative thereof of the peptide/polynucleotide conjugate-bonds through hydrogen bonding with the polysaccharide having the β-1,3-glucan backbone, and forms a complex having a triple helix structure including one molecular chain of the polynucleotide or derivative thereof and two molecular chains of the polysaccharide having the β-1,3-glucan backbone.

In the peptide/β-1,3-glucan complex according to the second aspect of the present disclosure, the polysaccharide having the β-1,3-glucan backbone is preferably schizophyllan, lentinan, scleroglucan, or curdlan.

In the peptide/β-1,3-glucan complex according to the second aspect of the present disclosure, the polynucleotide or derivative thereof may be poly-deoxyadenosine.

In the peptide/β-1,3-glucan complex according to the second aspect of the present disclosure, the polynucleotide or derivative thereof is preferably a polynucleotide derivative in which at least a portion of phosphodiester bonds of DNA or RNA is substituted with a phosphorothioate group.

In the peptide/β-1,3-glucan complex according to the second aspect of the present disclosure, at least 50% of the phosphodiester bonds may be substituted with the phosphorothioate group.

In the peptide/β-1,3-glucan complex according to the second aspect of the present disclosure, the polynucleotide or derivative thereof and the antigenic peptide included in the peptide/polynucleotide conjugate may be bonded through conjugate bonds formed by: a cycloaddition reaction between an alkyne and an azide derivative, a reaction between a maleimide group and a thiol group, or a reaction between a thiol group of a thiol-modified nucleic acid and a thiol group of a peptide C-terminal cysteine residue.

An third aspect of the present disclosure solves the above-described problem by providing a peptide/β-1,3-glucan complex that includes:
  a polysaccharide having a β-1,3-glucan backbone; and
  an antigenic peptide bonded to a main chain of the polysaccharide having the β-1,3-glucan backbone, or bonded to a glucose residue on a side chain of the polysaccharide having the β-1,3-glucan backbone, wherein
  the bonding is covalent bonding formed by a cycloaddition reaction between an alkyne and an azide derivative, or by a reaction between a thiol group and a maleimide group or vinyl sulfone group.

In the peptide/β-1,3-glucan complex according to the third aspect of the present disclosure, the polysaccharide having the β-1,3-glucan backbone is preferably schizophyllan, lentinan, scleroglucan or curdlan.

According to an fourth aspect of the present disclosure, in the peptide/β-1,3-glucan complex according to the first to third aspects of the present disclosure, the peptide/β-1,3-glucan complex further includes a polynucleotide or derivative thereof having a partial base sequence having immunostimulatory activity; and the polynucleotide or derivative thereof and the polysaccharide having the β-1,3-glucan backbone are bonded by hydrogen bonding to form a complex having a triple helix structure including two molecular chains of the polysaccharide having the β-1,3-glucan backbone and one molecular chain of the polynucleotide or derivative thereof.

In the peptide/β-1,3-glucan complex according to the fourth aspect of the present disclosure, a portion of the polynucleotide or derivative thereof forming the complex having the triple helix structure is preferably poly-deoxyadenosine.

In the peptide/β-1,3-glucan complex according to the fourth aspect of the present disclosure, the portion of the polynucleotide or derivative thereof forming the complex having the triple helix structure is preferably a polynucleotide derivative in which at least a portion of phosphodiester bonds of DNA or RNA is substituted with a phosphorothioate group.

In the peptide/β-1,3-glucan complex according to the fourth aspect of the present disclosure, the polynucleotide derivative in which the portion of phosphodiester bonds of DNA or RNA is substituted with a phosphorothioate group, may have at least 50% of the phosphodiester bonds substituted with the phosphorothioate group.

An fifth aspect of the present disclosure solves the above-described problem by providing a method for production of a peptide/β-1,3-glucan complex, wherein
  the peptide/β-1,3-glucan complex includes:
  a polysaccharide having a β-1,3-glucan backbone; and
  a peptide/polynucleotide conjugate in which an antigenic peptide is bonded covalently to a polynucleotide or derivative thereof, wherein
  the covalent bonding is formed by a cycloaddition reaction between an alkyne and an azide derivative, a reaction between a thiol group and a maleimide group or vinyl sulfone group or a reaction between a thiol group of a thiol-modified nucleic acid and a thiol group of a peptide C-terminal cysteine residue; wherein
  the polynucleotide or derivative thereof of the peptide/polynucleotide bonds through hydrogen bonding with the polysaccharide having the β-1,3-glucan backbone, and forms a complex having a triple helix structure including one molecular chain of the polynucleotide or derivative thereof and two molecular chains of the polysaccharide having the β-1,3-glucan backbone; and
  the method includes the step of liquid chromatographic separating of the peptide/polynucleotide conjugate in the presence of a chelating agent.

In a sixth aspect of the present disclosure, the above-described problem is solved by providing a pharmaceutical composition that includes:
  a polynucleotide or derivative thereof having a partial base sequence having immunostimulatory activity, and
  the peptide/β-1,3-glucan complex according to the first to third aspects of the present disclosure.

In the pharmaceutical composition according to the sixth aspect of the present disclosure, the polynucleotide or derivative thereof and the polysaccharide having the β-1,3-glucan backbone may be bonded by hydrogen bonding to form a complex having a triple helix structure including two molecular chains of the polysaccharide having the β-1,3-glucan backbone and one molecular chain of the polynucleotide or derivative thereof.

In the pharmaceutical composition according to the sixth aspect of the present disclosure, the polysaccharide having the β-1,3-glucan backbone included in the polynucleotide/β-1,3-glucan complex is preferably schizophyllan, lentinan, scleroglucan, or curdlan.

In an seventh aspect of the present disclosure, the above-described problem is solved by providing a pharmaceutical composition that includes the peptide/β-1,3-glucan complex of the fourth aspect of the present disclosure.

Advantageous Effects of Invention

Advantageous effects, such as those listed below, are obtained according to the present disclosure.

(1) According to the type, molecular weight, combination and the like of the β-1,3-glucan and the antigenic peptide; mode of bonding between the β-1,3-glucan and the antigenic peptide can be selected among covalent bonding between the β-1,3-glucan and the antigenic peptide, and hydrogen bonding between the β-1,3-glucan and the polynucleotide or derivative thereof of the peptide/polynucleotide conjugate. Thus peptide/β-1,3-glucan complexes can be obtained from a wide range of combinations of the β-1,3-glucan and the antigenic peptide.

(2) By use of the cycloaddition reaction between an alkyne and an azide derivative, or the reaction between a maleimide group and a thiol group (Michael addition reaction), in the reaction to produce the covalent bond between the β-1,3-glucan and the antigenic peptide, the reaction can be performed quickly and with high yield, even in a polar solvent containing water. Thus the peptide/β-1,3-glucan complex can be obtained with a high yield in a short time period, and the effort of isolation and purification can be reduced. Thus productivity in the production of the peptide/β-1,3-glucan complex of the present disclosure is excellent, and the peptide/β-1,3-glucan complex can be produced at low cost.

(3) By use of the peptide/β-1,3-glucan complex of the present disclosure, induction of the immune response specific for the antigenic peptide can be more effectively performed in comparison to when the antigenic peptide is used alone.

(4) The immune response can be more effectively induced by use of, as the peptide/β-1,3-glucan complex of the present disclosure, the peptide/β-1,3-glucan complex that further includes a polynucleotide or derivative thereof having a partial base sequence having immunostimulatory activity; wherein the polynucleotide or derivative thereof and the polysaccharide having the β-1,3-glucan backbone are bonded by hydrogen bonding to form a complex having a triple helix structure including two molecular chains of the polysaccharide having the β-1,3-glucan backbone and one molecular chain of the polynucleotide or derivative thereof.

(5) By use of the pharmaceutical composition including peptide/β-1,3-glucan complex of the present disclosure, an immune response reaction can be induced, with specificity over a broad range of antigenic peptides, more effectively than when the antigenic peptide is used alone. Thus use can be anticipated as a vaccine and/or immunostimulant.

DESCRIPTION OF EXAMPLES

Figure 1:
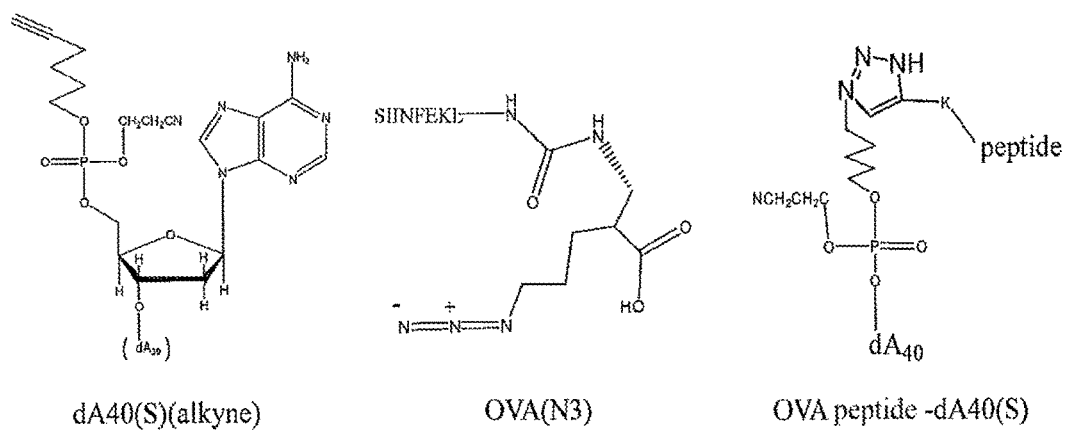
FIG. 1 shows chemical structures of dA40(S)(alkyne) and OVA(N3) in an Example 1 of the present disclosure.

Specific embodiments of the present disclosure are described below to provide understanding of the present disclosure. The peptide/β-1,3-glucan complex in the first embodiment of the present disclosure includes a polysaccharide having the β-1,3-glucan backbone (β-1,3-glucan), and a peptide/polynucleotide conjugate in which a peptide having antigenicity (antigenic peptide) is bonded covalently with a polynucleotide or derivative thereof. The polynucleotide or derivative thereof of the peptide/polynucleotide conjugate forms, through hydrogen bonding with the β-1,3-glucan, a complex having a triple helix structure, and including one molecular chain of the polynucleotide or derivative thereof and two molecular chains of the β-1,3-glucan.

(1) β-1,3-Glucan

No particular limitation is placed on the type or molecular weight of the utilized β-1,3-glucan, as long as a complex can be formed that includes one molecular chain of the polynucleotide or derivative thereof and two molecular chains of the β-1,3-glucan. The polysaccharide having the β-1,3-glucan backbone has helical parameters resembling those of nucleic acids such as poly(C) and the like (for example, see Prog. Polym. Phys. Jpn. 27, p. 767; and "Conformation of Carbohydrates", Sharwood Academic Publisher, 1998), and also has hydroxyl groups that are capable of hydrogen-bonding with nucleic acid bases. Thus such polysaccharides and nucleic acids are known to interact with one another and to form a stable complex that has a helical structure. Specific examples that can be cited of β-1,3-glucan include schizophyllan, curdlan, lentinan, pachyman, grifolan, scleroglucan and the like. These are glucans in which the main chain is formed by β-bonding (β-D-bonding), and are natural polysaccharides having different frequencies of side chains. Although such β-1,3-glucans may be used without undergoing treatment such as chemical decoration and the like, the normal periodate oxidation method can be used to reduce the number of side chains in order to control solubility.

Molecular weight of β-1,3-glucan is adjusted appropriately according to base sequence, base length and the like of the polynucleotide or derivative thereof included in the peptide/nucleotide conjugate. However, when the molecular weight is low, expression of the so-called cluster effect, a cooperative-emergent phenomenon in polymer systems, becomes difficult, and such low molecular weight is undesirable. Although single-chain weight average molecular weight of β-1,3-glucan capable of forming a complex with the nucleic acid will vary according to the types of bases and higher-order structure of the nucleic acid, the weight average molecular weight is preferably greater than or equal to 2,000, further preferably is greater than or equal to 4,000, and most preferably is greater than or equal to 6,000. Moreover, the desired number of hydroxyl groups forming hydrogen bonds with the nucleic acid bases on the polynucleotide is normally at least 5 groups, is preferably at least 8 groups, and further preferably is at least 10 groups.

Furthermore, the weight average molecular weight of β-1,3-glucan can be determined by use of any widely-known method, such as optical scattering, settling rate (centrifugal method) and the like.

Since β-1,3-glucan can be generally produced by fungi and bacteria, β-1,3-glucan can be obtained by culturing such microorganisms, homogenizing the fungus body, and then using ultracentrifugation and the like methods to isolate the β-1,3-glucan from impurities such as cellular eluate, undissolved residue and the like. Generally the β-1,3-glucan obtained in this manner assumes a triple helical structure with a high molecular weight, such as a weight average molecular weight of roughly several tens of thousands. As may be required, molecular weight reduction may be used. Molecular weight reduction is performed by selection of suitable conditions and a method, such as enzymatic decomposition, hydrolysis and the like, according to the type and desired molecular weight of the β-1,3-glucan. For example, in the case of schizophyllan, by a method such as hydrolysis using 80% DMSO-sulfuric acid, single-chain schizophyllan can be obtained that has various molecular weight values.

(2) Peptide/Polynucleotide Conjugate

The peptide/polynucleotide conjugate is a complex formed through covalent bonding between the antigenic peptide and the polynucleotide or derivative thereof. The polynucleotide or derivative thereof bonded to the antigenic peptide, in the above-described manner, plays the role of bonding together the antigenic peptide and the β-1,3-glucan by causing the formation of the complex having the triple helical structure with the β-1,3-glucan.

Any peptide having antigenicity can be used as the "antigenic peptide", without particular limitation on the amino acid sequence or number of amino acid residues, as long as the antigenic peptide is recognized as foreign by the body's immune system, and causes the production of antibodies specific to the peptide. Among proteins derived from proteins causing allergies such as food allergies and the like, pathogens such as bacteria, viruses and the like, tumor cells and the like, proteins may be cited, as the antigenic peptide used for the production of the peptide/β-1,3-glucan complex according to the present example, that have partial amino acid sequences capable of use as epitopes. Although no particular limitation is placed on the number of amino acid bases forming the antigenic peptide capable of use as the epitope, the number of amino acid bases in many cases is within the range of 5 to 30 bases, and in most cases is in the range of about 8 to 17 bases.

The antigenic peptide can be obtained by any know method, such as enzymatic decomposition of the source protein, peptide synthesis and the like. Moreover, the amino acid sequence of the antigenic peptide can be determined using any know method, such as epitope analysis using a peptide array and the like.

No particular limitation is placed on the polynucleotide or derivative thereof, which may have any base sequence and number of bases, for bonding with the antigenic peptide, as long as the polynucleotide or derivative thereof forms a triple helical structure-type complex with β-1,3-glucan in the above described manner. Specific examples of polynucleotides that can be cited include polyriboadenylic acid (polyA), polyribocytidylic acid (polyC), polydeoxyadenylic acid (poly(dA)) and polydeoxythymidylic acid (poly(dT)) capable of bonding with β-1,3-glucan. Although no particular limitation is placed on the number of polynucleotide bases, as long as the polynucleotide is capable of forming the triple helical structure-type complex with β-1,3-glucan in the above-described manner, in order to improve the ability to form the complex, the polynucleotide preferably has a repeating sequence capable of bonding with β-1,3-glucan, such as that of polyriboadenylic acid (polyA), polyribocytidylic acid (polyC), polydeoxyadenylic acid (poly(dA)) or polydeoxythymidylic acid (poly(dT)). The bases forming the desired repeat base sequence and the types and base count of the nucleotide are selected appropriately according to length of the ribonucleotide part, type and molecular weight of the utilized β-1,3-glucan and the like. For example, when schizophyllan is used as the β-1,3-glucan, the polydeoxynucleotide part preferably has a poly(dA) sequence as the repeating sequence. Due to difficulty in the formation of the triple helical structure by hydrogen bonding with β-1,3-glucan when the number of bases is low, length of the repeat sequence is required to be at least 10 bases, preferably is 20 to 80 bases, and further preferably is 30 to 80 bases.

Since polynucleotides are readily decomposed by nucleases within the body, a polynucleotide derivative may be used instead of the polynucleotide in order to improve in vivo stability. Cited examples of the polynucleotide derivative include derivatives in which part or all of the 2' position hydroxyl groups of the ribonucleotide are replace by methoxy groups, derivatives in which part or all of the phosphodiester groups of polyribonucleotide (RNA) or polydeoxyribonucleotide (DNA) are replaced by the phosphorothioate group, and the like. When part of the phosphodiester groups of the polyribonucleotide or polydeoxyribonucleotide is replaced by the phosphorothioate group, at least 50% of the phosphodiester bonds are preferably replaced by the phosphorothioate group. No particular limitation is placed on the position of the phosphodiester group replaced by the phosphorothioate group, and replacement may be performed such that multiple adjacent phosphodiester groups are replaced, or such that the phosphorothioate groups are mutually non-adjacent.

The polynucleotide or derivative thereof may bond to the N terminus, C terminus, or any side chain of the antigenic peptide. Bonding to either type of site may be performed by direct bonding by reaction between suitable reactive functional groups, and may be performed through a suitable spacer. The reactive functional group may be present on the unmodified antigenic peptide and the polynucleotide or derivative thereof, or the reactive functional group may be formed on the unmodified antigenic peptide and the polynucleotide or derivative thereof by activation by chemical decoration, or a suitable reactive functional group may be introduced. Moreover, the 5'-terminus side or the 3'-terminus side of the polynucleotide or derivative thereof may bond with the antigenic peptide.

As shown in the Formula (A) below, one preferred example of the peptide/polynucleotide conjugate has a structure in which the 5'-terminus side of phosphorothioated polydeoxyadenylic acid (polynucleotide derivative in which the phosphodiester group of polyA is replaced by the phosphorothioate group) is bonded to the C-terminus side of the peptide.

$$[\text{antigenic peptide}]\text{-X-}(dA(S))_x \qquad (A)$$

Furthermore, in Formula (A), dA(S) indicates phosphorothioated polydeoxyadenylic acid, and x is an integer greater than or equal to 20 and less than or equal to 80. X indicates a spacer or a functional group that is formed by reaction between reactive functional groups. One example of a spacer includes alkyl groups, polyethylene glycol (PEG) and the like. Cited examples of combinations of reactive functional groups include combinations of reactive functional groups used in fixing biomolecules to biochip surfaces, and more specific examples of such combinations are indicated below.

(a) Alkynes and Azide Compounds

The alkyne and azide compound form a 1,2,3-triazole ring by cycloaddition reaction, that is, Huisgen reaction, in the below indicated manner. Both reactants are stable functional groups capable of introduction to many organic compounds, including biomolecules. The reaction is rapid and nearly quantitative, even in a water-containing solvent. The reaction is nearly unaccompanied by the generation of byproducts, and almost no excess waste products are generated. Thus this reaction is widely used in the field of biochemistry as a central reaction of so-called "click chemistry". The alkyne derivative and the azide group can be introduced to the antigenic peptide, or to the polynucleotide or polynucleotide derivative, by use of any known method. An alkyne derivative can be easily obtained that has a reactive functional group, such as propargyl alcohol, propargylamine and the like, and this alkyne derivative can be reacted directly with a reactive functional group such as the carboxyl group, hydroxyl group and the like, or alternatively, the alkyne derivative can be introduced through a urethane bond, ester bond, amide bond and the like generated by reaction with carbonyldiimidazole and the like. Any known method can be used for introduction of the azide group to the antigenic peptide or to the polynucleotide or derivative thereof. Furthermore, although the Husigen reaction is performed in the presence of a copper catalyst, activity of the copper catalyst may decrease due to the presence of copper ion-coordinating sulfur atoms in the antigenic peptide and in the polynucleotide derivative in which the phosphodiester group is substituted with a sulfur-containing functional group such as the phosphorothioate group and the like. An excess amount of copper is preferably added in order to improve the reaction rate.

[Formula 1]

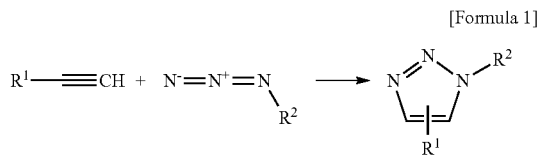

(b) Thiol Group and Maleimide or Vinyl Sulfone

At pH in the vicinity of neutral, a vinyl sulfone or maleimide having a double bond adjacent to an electron-accepting carbonyl group or sulfone group generates a stable thioester derivative by addition reaction with the thiol group (Michael addition reaction) as indicated below. Maleimide and vinyl sulfone derivatives having a suitable spacer are commercially marketed, and thus these reactive groups are easily introduced to the antigenic peptide or to the polynucleotide or derivative thereof. When a thiol group is introduced to the antigenic peptide, a thiol group of the cysteine residue side chain can be used when the antigenic peptide includes cysteine. However, cysteine is a low-abundance amino acid, and thus an antigenic peptide is used in which cysteine is introduced to the C-terminus side. Thiolated polynucleotides in which the thiol group replaces the 5'-terminus hydroxyl group are used as the polynucleotide or derivative thereof that includes the thiol group.

[Formula 2]

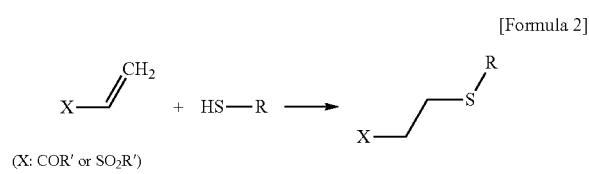

(X: COR' or SO₂R')

(c) Cysteine Side-Chain Thiol Group and Thiolated Polynucleotide Thiol Group

In the above manner, the thiol group of the cysteine residue side chain of the antigenic peptide having cysteine introduced to the C-terminus side and the thiol group of the thiolated polynucleotide are reacted to form a disulfide group. Since the disulfide bond is severed in the presence of a reducing agent, stability is inferior in comparison to both of the above combinations of reactive functional groups.

(3) Preparation of the Peptide/β-1,3-Glucan Complex

A β-1,3-glucan such as schizophyllan and the like normally has a triple helical structure in water. Thus in order to form the complex with the polynucleotide or derivative thereof, the polynucleotide or derivative thereof is dissolved in a solvent such as DMSO to use intermolecular hydrogen bonding and hydrophobic interaction to unravel the associated state of the β-1,3-glucan and to obtain a single chain. When an aqueous solution, or a solution of a polar solvent such as an alcohol and the like, containing polynucleotide is added, in accompaniment with the increase in polarity of the solvent, the β-1,3-glucan and polynucleotide aggregate together due to hydrophobic interaction, and while incorporating the polynucleotide molecular chain, an aggregate is formed intra-molecularly and inter-molecularly between the polynucleotide and the polysaccharide. As a result, a complex is formed that has a triple helical structure that includes one molecule of the polynucleotide or derivative thereof and two molecules of the β-1,3-glucan. Formation of the complex can be confirmed, for example, based on examination of conformational changes by measuring the circular dichroism (CD) spectrum.

The peptide/β-1,3-glucan complex according to the second embodiment of the present disclosure includes an antigenic peptide bonded to a glucose residue on the main chain or side chain of the polysaccharide having the β-1,3-glucan backbone via a covalent bond generated by reaction between the polysaccharide having the β-1,3-glucan backbone, as the cycloaddition reaction between the alkyne and azide derivative, or the reaction between the maleimide group or vinyl sulfone group and thiol group.

The β-1,3-glucan and the antigenic peptide used in the preparation of the peptide/β-1,3-glucan complex according to the present example are similar to those used in the preparation of the peptide/β-1,3-glucan complex according to the first embodiment of the present disclosure, and thus detailed explanation of the β-1,3-glucan and the antigenic peptide used in the preparation of the peptide/β-1,3-glucan complex according to the present embodiment is omitted. The β-1,3-glucan and the antigenic peptide are bonded covalently formed by the cycloaddition reaction between the alkyne and azide derivative, or the reaction between the maleimide group or vinyl sulfone group and the thiol group. Although the antigenic peptide may be bound to either the main chain or a side chain of the β-1,3-glucan molecule, in consideration of steric hindrance, the bonding is preferably with a glucose residue of a side chain. Moreover, although the antigenic peptide may bond to either the N-terminus side or the C-terminus side, or may bond with a side chain, in consideration of steric hindrance when contacting the antigen-presenting cell, bonding with the β-1,3-glucan preferably occurs at the N-terminus side or C-terminus side. The introduction of the alkyne derivative and azide group to the β-1,3-glucan and antigenic peptide can be performed using any known method, in the same manner as for the peptide/nucleotide conjugate in the preparation of the peptide/β-1,3-glucan complex according to the first embodiment of the present disclosure.

In the peptide/β-1,3-glucan complex according to a third embodiment of the present disclosure, the aforementioned peptide/β-1,3-glucan complexes according to the first or second embodiments of the present disclosure further include a polynucleotide or derivative thereof having a partial base sequence having immunostimulatory activity, and the polynucleotide or derivative thereof is bonded to the β-1,3-glucan through hydrogen bonding to form a complex (ternary complex including the antigenic peptide, β-1,3-glucan, and the polynucleotide or derivative thereof) having the triple helical structure formed from one molecular chain of the polynucleotide or derivative thereof and two molecular chains of the β-1,3-glucan.

The site for bonding through hydrogen bonding with β-1,3-glucan and within the antigenic peptide, β-1,3-glucan, polynucleotide or derivative thereof used in the preparation of the peptide/β-1,3-glucan complex according to the present example is the same as that used in the production of the peptide/β-1,3-glucan complex according to first or second embodiments of the present disclosure, and thus detailed further description of this bonding site is omitted.

Specific examples of partial base sequences having immunostimulatory activity, within the polynucleotide or derivative thereof, include: non-methylated CpG DNA derived from bacteria and viruses and activating immunity by "bridging" between innate immunity and acquired immunity through recognition by TLR9, double-stranded RNA derived from viruses for activating immunity by "bridging" between innate and acquired immunity by recognition by TLR3, virus genome RNA and artificial RNA for activating immunity by recognition by a RIG-I-like receptor (RLR), and the like.

The hybrid between the RNA or DNA having the aforementioned partial base sequence having immunostimulatory activity and the polynucleotide or derivative thereof having the partial base sequence bonded to β-1,3-glucan through hydrogen bonding can be obtained or synthesized using any known method. Furthermore, when the polynucleotide or derivative thereof is a chimeric nucleic acid having the RNA 5'-terminus side bonded to the DNA 3'-terminus side, due to the phosphodiester bond between the RNA and DNA readily undergoing decomposition, durability of the bond against hydrolysis is preferably improved by derivatizing, such as by using a methyl or fluoro group to replace the hydroxyl group of the 2' position in the 5'-terminus side nucleotide of the RNA bonded to the DNA and/or using a phosphorothioate group to replace the phosphodiester group between the 3' position of the initial ribonucleotide bonded to the DNA and the 5' position of the RNA adjacent thereto.

The peptide/β-1,3-glucan complex according to the present embodiment is prepared by any one of the below listed methods.

(1) The aforementioned β-1,3-glucan, peptide/nucleotide conjugate and the polynucleotide or derivative thereof are complexed using the same method as that of the preparation method of the peptide/β-1,3-glucan complex of the Example 1 of the present disclosure.

(2) The peptide/β-1,3-glucan complex and the polynucleotide or derivative thereof according to the second embodiment of the present disclosure are complexed using the same method as that in the preparation method of the peptide/β-1,3-glucan complex according to the first embodiment of the present disclosure.

The pharmaceutical composition according to fourth embodiment of the present disclosure (abbreviated below as the "pharmaceutical composition") includes the peptide/β-1,3-glucan complex according to the first or second embodiments of the present disclosure, or the peptide/β-1,3-glucan complex according to the Example 3 of the present disclosure, and includes the polynucleotide/β-1,3-glucan complex having the triple helical structure including two molecular chains of the polysaccharide having the β-1,3-glucan backbone and one molecular chain of the polynucleotide or derivative thereof, the polynucleotide/β-1,3-glucan complex being formed by hydrogen bonding between the β-1,3-glucan backbone and the polynucleotide or derivative thereof having the partial base sequence having immunostimulatory activity.

Except for using the peptide/nucleotide conjugate in place of the nucleotide or polynucleotide derivative, the polynucleotide/β-1,3-glucan complex is prepared using the same method as that of the peptide/β-1,3-glucan complex according to the first embodiment of the present disclosure.

Any known components (such as any pharmacologically permissible carrier, excipient and additive) and preparation methods and be used in the preparation of the pharmaceutical composition, in addition to the polynucleotide/β-1,3-glucan complex and the peptide/β-1,3-glucan complex as the effective ingredient. For example, the pharmaceutical composition can assume the form of a tablet, suppository, capsule, syrup, nanogel and the like microcapsule, sterilized solution, suspension liquid and the like injection solution, aerosol, spray and the like.

The pharmaceutical composition can be orally or parenterally administered to humans or warm blooded animals, such as mice, rats, rabbits, sheep, pigs, cattle, horses, chickens, cats, dogs, monkeys and the like. Examples of parenteral administration include subcutaneous injection, intradermal injection, intramuscular injection, intraperitoneal administration, intravenous administration, nasal mucous membrane spray administration, pharyngeal region spray administration and the like.

The dose of the peptide/β-1,3-glucan complex and polynucleotide/β-1,3-glucan complex active ingredient will differ depending on activity, the disease undergoing medical treatment, and the type, body weight, sex, and age of the animal undergoing treatment, severity of the disease, treatment method and the like. In the case of oral administration to an adult weighing 60 kg, the daily dose is generally about 0.1 mg to about 100 mg, preferably is about 1.0 mg to about 50 mg, and more preferably is about 1.0 mg to about 20 mg. In the case of parenteral administration, the daily dose is generally about 0.01 mg to about 30 mg, preferably is about 0.1 mg to about 20 mg, and more preferably is about 0.1 mg to about 10 mg. In the case of administration to an animal (non-human), the used dose is calculated by converting the aforementioned dose to a dose per unit body weight and then multiplying by body weight of the animal undergoing treatment.

By activation of immunity, the pharmaceutical composition can be used as a vaccine and the like for treatment or prevention of infective diseases caused by infection by pathogens such as bacteria, viruses and the like, and for treatment or prevention of tumors such as cancerous tumors and the like.

EXAMPLES

Examples are provided below for confirmation of the effect of use of the present disclosure.

Example 1: Preparation of Antigenic Peptide/Polynucleotide Conjugate

In the present example, preparation was investigated of an antigenic peptide/polynucleotide conjugate (referred to hereinafter as "OVA peptide-dA40(S)") of a polynucleotide adduct (referred to hereinafter as "dA40(S)(alkyne)") having an alkyne introduced at the 5' side of a polynucleotide derivative (referred to hereinafter as "dA40(S)") having a structure in which phosphorothioate bonds replaced all phosphodiester bonds in deoxyadenine 40-mer and an antigenic peptide (referred to hereinafter as "OVA(N3)") obtained by introduction of an azide group to the C terminus of ovalbumin ((OVA)-derived antigenic peptide, amino acid sequence: SIINFEKL (SEQ ID No. 1), obtained from Gene Design Inc.). Each chemical structure is shown in FIG. 1.

OVA(N3) (using water plus DMSO as solvent, 10 μM to 800 μM final concentration), dA40(S)(alkyne) (using water as solvent, 10 μM final concentration), Cu(II) sulfate pentahydrate (using water as solvent, 1.5 mM final concentration), sodium ascorbate (using water as solvent, 3.0 mM final concentration), and (tris(1-benzyl-1H-1,2,3-driazo-4-yl)methyl)amine (using DMSO as solvent, 0.6 mM final concentration) were blended, and a "click chemistry" reaction was performed using copper catalyst for 1 hour at room temperature. After the reaction, a sample solution was diluted using a chelating agent solution of pH 7.4 ethylenediaminetetraacetate (EDTA) (final concentration of at least 20 mM), and then HPLC analysis was performed. Due to difficulty of elution due to strong mutual interaction between dA40(S) and the HPLC column, elution was made easier by addition of EDTA to weaken the mutual interaction.

Figure 2:
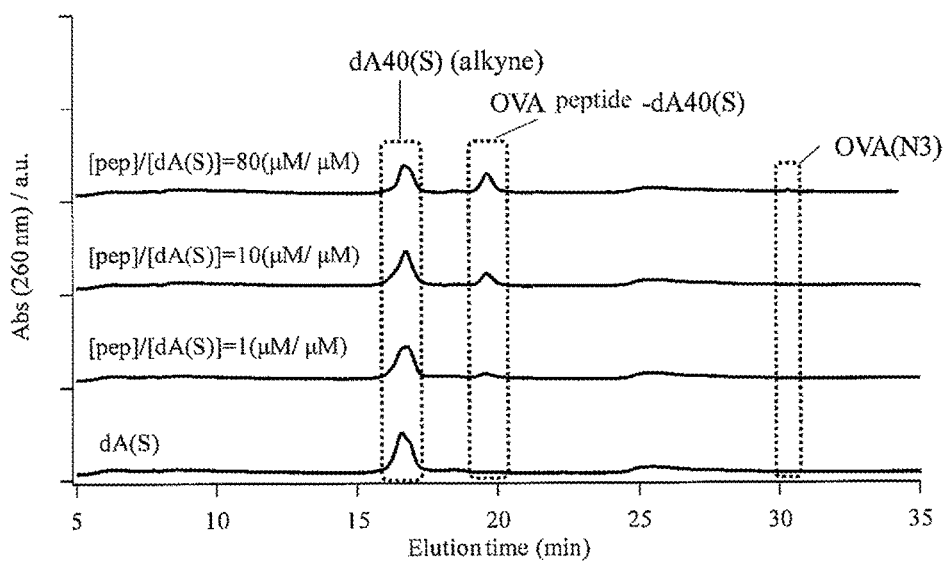
FIG. 2 is an HPLC chromatogram showing results of production of an antigenic peptide/polynucleotide conjugate in the Example 1.

In the HPLC analysis, an Inertsil ODS-3 (GL Sciences Inc.) was used as the column, 0.1 M trimethylamine/acetate (TEAA) buffer (pH 7.0) and acetyl nitrile was used as the eluent, and a diode array was used as the detector. Change of UV absorption by dA40(S)(alkyne) was tracked at 260 nm. The results are shown in FIG. 2. Peptide amount-dependent shift was confirmed for the dA40(S)(alkyne) peak from the vicinity of 17 minutes to the vicinity of 20 minutes due to the addition of the peptide. In measurement using a reverse phase column, elution time became delayed, suggesting that the molecule had become more hydrophobic. Based on these results, OVA peptide-dA40(S) was understood to have been generated.

Example 2: Complex Between Antigenic Peptide/Polynucleotide Conjugate and Polysaccharide Having β-1,3-Glucan Backbone In the present example, schizophyllan (SPG) used as the polysaccharide having the β-1,3-glucan backbone was obtained by the method described in the examples of Unexamined Japanese Patent Application Kokai Publication No. 2010-174107. This was purified using a certain method. GPC was used to determine molecular weight as 150,000 for the single strand and 450,000 for the triple strand. Testing was performed using the complex of this SPG and the OVA peptide-dA40(S) prepared in Example 1.

Although a β-1,3-glucan such as SPG and the like disassociates into single strands in an alkaline aqueous solution in the above-described manner, when the β-1,3-glucan-including solution is neutralized by addition of phosphate buffer solution, three molecules of the β-1,3-glucan become mutually associated through hydrogen bonding, and the triple helical structure is regenerated. The inventers discovered that, when the polynucleotide or derivative thereof, such as dA40(S) and the like, was present in the mixture, one molecule of the polynucleotide or derivative thereof and two molecules of the β-1,3-glucan became mutually associated through hydrogen bonding and hydrophobic interaction to generate the complex having the triple helical structure. In the present example, investigation was performed to see whether a complex was generated that had the same type of triple helical structure, even when dA40(S), which is one example of the polynucleotide or derivative thereof, was combined with SPG and an antigenic peptide-dA40(S).

SPG was dissolved (15 mg/mL) in 0.25N NaOH solution, and the mixture was allowed to sit for 2 days in order to allow complete disassociation into single strands. A 10% dimethyl sulfoxide (DMSO) aqueous solution (solution using as a solvent water including 10 volume percent DMSO, same hereinafter) of OVA peptide-dA40(S) and a phosphate buffer solution (330 mM $NaH_2PO_4$, pH 4.5) were mixed, the aforementioned SPG solution was added, and the mixture was stirred. Furthermore, concentrations of each of the solutions were adjusted so that molar mixing ratio of SPG to OVA peptide-dA40(S) became 3:1, and volume ratio of the SPG solution to phosphate buffer solution became 1:1. After the reaction mixture was allowed to sit overnight at 4° C., the reaction mixture was stirred, and then acrylamide gel electrophoresis was performed. Acrylamide gel electrophoresis of the antigenic peptide-dA40(S) was also performed for comparison.

Figure 3:
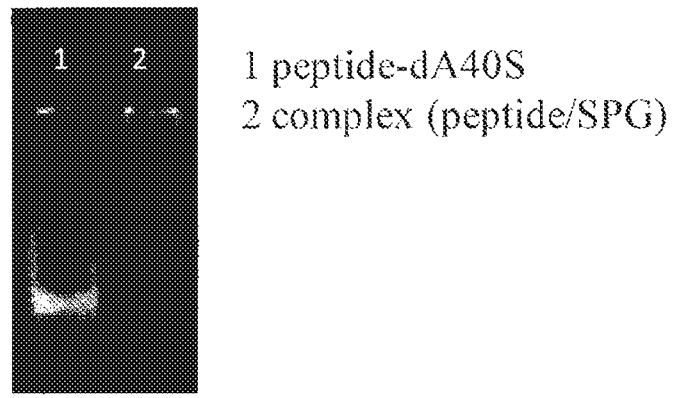
FIG. 3 is a gel electrophoresis image showing results of complexing between an antigenic peptide-dA40(S) and SPG in an Example 2.

FIG. 3 shows the result of fluorescence imaging after using SYBR Gold to stain the acrylamide gel after electrophoresis. Disappearance of the band of the OVA peptide-dA40(S) measured at lane 1 (peptide-dA40(S)) was confirmed by the lane of the stirred reaction mixture (lane 2: complex (peptide/SPG)). Based on these results, the OVA peptide-dA40(S) was understood to have complexed with SPC, and a complex was understood to be generated that had a higher molecular weight (OVA peptide-dA40(S)/SPG complex).

Example 3: Effect of Complex Between Antigenic Peptide and SPG in Antigen-Specific Immune Response to Antigenic Peptide in Mouse Spleen Cells (1) One of the following was intradermally administered once to mice (C57BL/6 mouse, male, 7 weeks old): (1) antigenic peptide (OVA peptide, 5 μg) having an ovalbumin (OVA)-derived amino acid sequence (SEQ ID No. 1), (2) ovalbumin (5 μg) and CpG DNA (base sequence: ATC-GACTCTCGAGCGTTCTC (SEQ ID No. 2), 30 μg), (3) OVA peptide-dA40(S)/SPG complex (see Example 1, 5 μg), (4) OVA peptide-dA40(S)/SPG complex (prepared as in Example 1, 5 μg) and CpG DNA (30 μg), and (5) OVA peptide-dA40(S)/SPG complex (5 μg) and incomplete Freund's adjuvant (IFA). An investigation was performed to see whether antigen-specific interferon-γ (IFN-γ) was induced by, one week after administration, harvesting spleen cells from the mice, placing the cells in 96 wells ($1.0 \times 10^6$ cells/well), and then stimulating the cells using OVA peptide (10 μg/mL).

Figure 4:
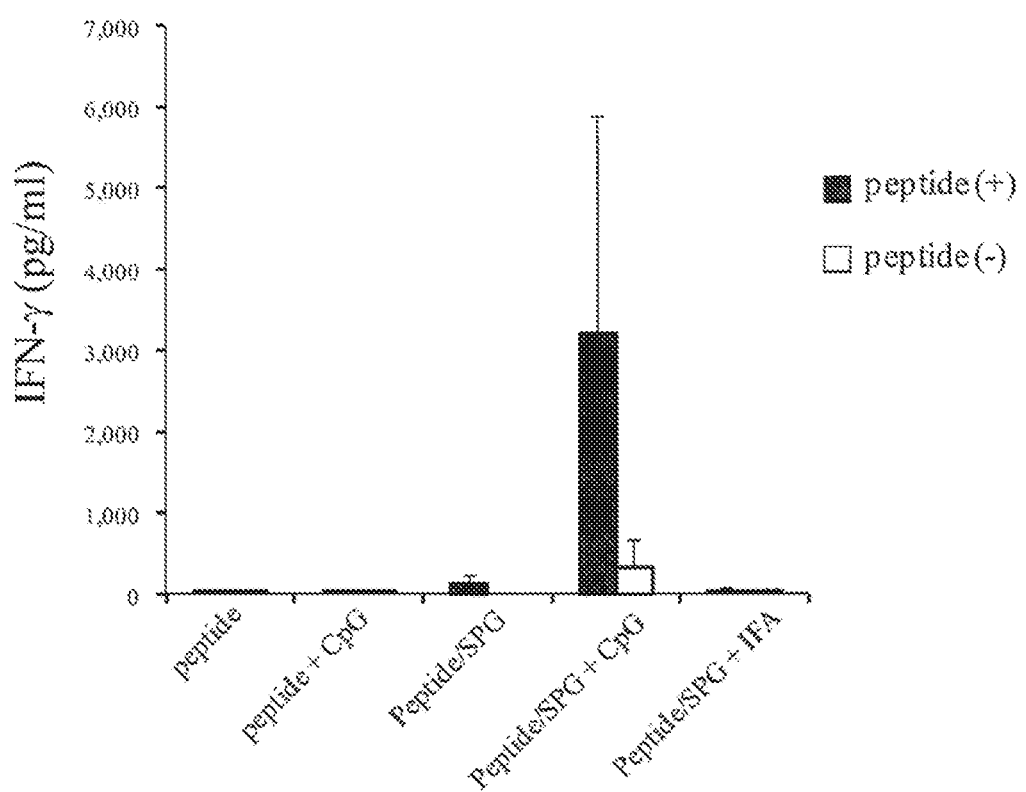
FIG. 4 is a graph showing determination of an amount of produced antigenic peptide-specific IFN-γ produced by using an antigenic peptide to stimulate spleen cells of mice, in which immunity is induced by various samples in an Example 3.

Then 24 hours after stimulating the spleen cells by OVA peptide, enzyme-linked immunosorbent assay (ELISA) was used to quantitatively measure IFN-γ in the culture medium. Results are shown in FIG. 4. No OVA peptide-specific interferon reaction was observed in the case of administration of OVA peptide alone, in the case of simultaneous administration of OVA peptide and CpG DNA, and in the case of administration of OVA peptide-dA40(S)/SPC complex alone. This reaction was extremely weak in the case in which the OVA peptide-dA40(S)/SPG complex was administered simultaneously with the incomplete Freund's adjuvant (IFA), which is a commercial adjuvant. However, the ability to induce a strong immune response (increase of produced amount of IFN-γ) could be confirmed in the case of simultaneous administration of OVA peptide-dA40(S)/SPG complex and CpG DNA. This ability is thought to occur because, although removal from the body was rapid in the case of administration of the OVA peptide alone, by allowing OVA peptide-dA40(S) to complex with SPG, uptake by antigen-presently cells was promoted, and thus by TLR9 being stimulated by the CpG DNA, the fraction of antigen-specific T cells increased.

Example 4: Evaluation of Effect of Complexing Between Antigenic Peptide and SPG on Inducibility of Antigenic Peptide-Specific Cytolytic T-Lymphocytes Mouse spleen cells were harvested from mice to which had been intradermally administered in Example 3 the (1) OVA peptide, (2) OVA peptide and CpG DNA, (3) OVA peptide-dA40(S)/SPG complex, or (4) OVA peptide-dA40(S)/SPG complex and CpG DNA. The harvested cells were stimulated using OVA peptide-dA40(S)/SPG complex and were cultured for 6 days. Then after antibody staining, a flow cytometer was used to evaluate the fraction of T cells that had cytotoxic specificity (CD8 positive) for OVA peptide.

Figure 5:
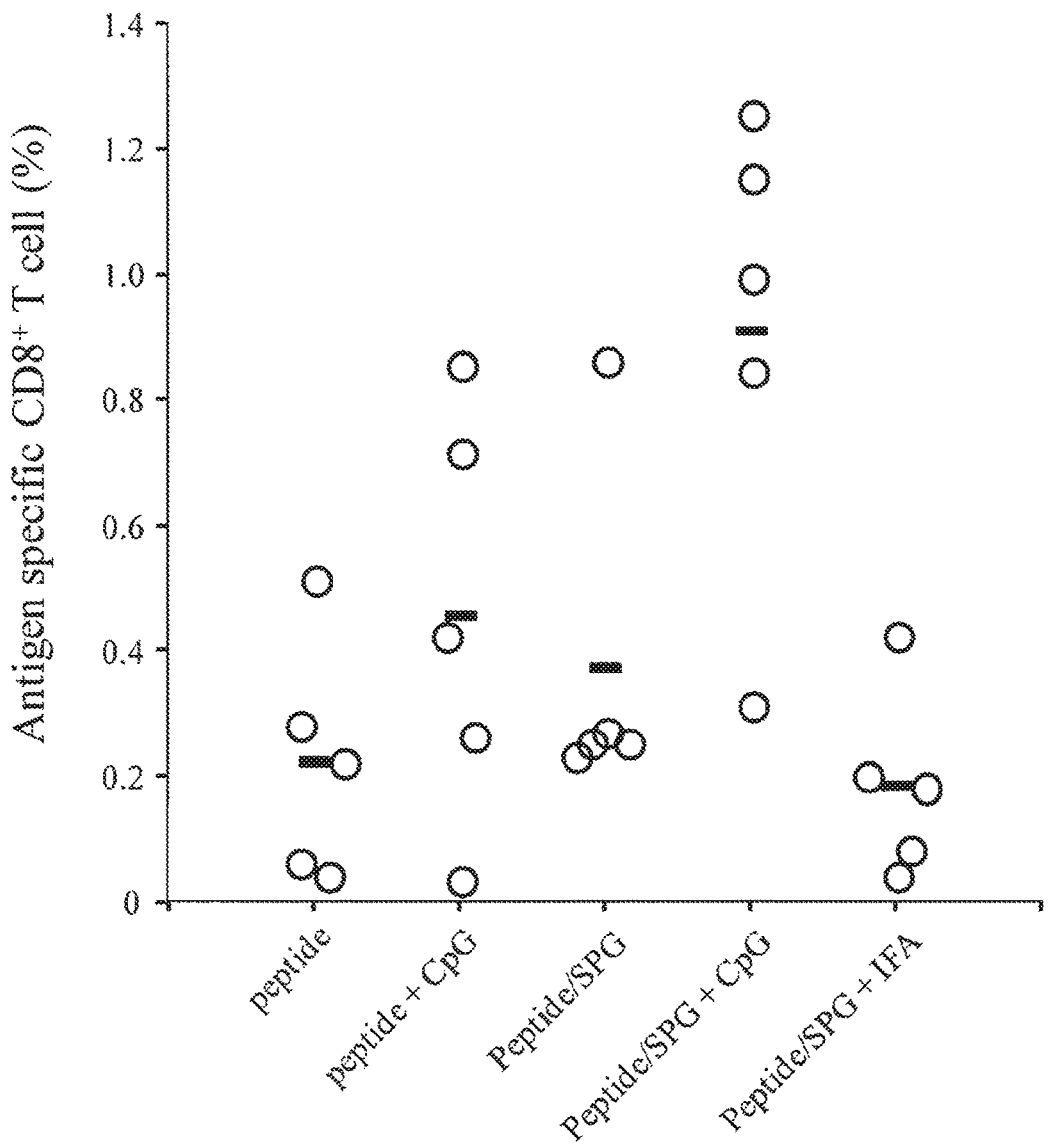
FIG. 5 is a graph showing a fraction of antigenic peptide-specific cytolytic T-lymphocytes, grown by using an antigenic peptide to stimulate spleen cells of mice, in which immunity is induced by various samples in an Example 4.

The fraction of CD8-positive T cells specific for OVA peptide among the spleen cells is shown in FIG. 5. The fraction of OVA peptide-specific CD8-positive T cells was low for the case (peptide) in which OVA peptide alone was administered, the case (peptide+CpG) in which OVA peptide and CpG DNA were simultaneously administered, and the case (peptide/SPG) in which OVA peptide-dA40(S)/SPG complex alone was administered. However, a significant increase in the fraction of CD8-positive T cells specific for OVA peptide was confirmed in the case (peptide/SPG+CpG) in which OVA peptide-dA40(S)/SPG complex was administered simultaneously with CpG DNA.

Example 5: Complexing Between Antigenic Peptide, Polynucleotide Derivative Having Partial Base Sequence Having Immunostimulatory Activity, and Polysaccharide Having the β-1,3-Glucan Backbone An investigation was conducted concerning simultaneous complexing between SPG, OVA peptide-dA40(S) and CpG DNA-dA40(S).

SPG was dissolved (15 mg/mL) in 0.25N NaOH solution, and the solution was allowed to sit for at least 2 days for complete disassociation into single strands. An aqueous solution of CpG DNA-dA40(S) (polynucleotide derivative having a structure in which dA40(S) was bonded to the 3'-terminus side of CpG DNA), a 10% DMSO aqueous solution of OVA peptide-dA40(S), and a phosphate buffer solution (330 mM $NaH_2PO_4$, pH 4.5) were mixed together, the aforementioned SPG solution was added, and the mixture was stirred. The concentrations of each of the solutions were adjusted such that molar ratios of the SPG to OVA peptide-dA40(S) and the SPG to CpG DNA-dA40(S) were both 3:1, and the volume ratio of the SPG solution to the phosphate buffer solution became 1:1.

Figure 6:
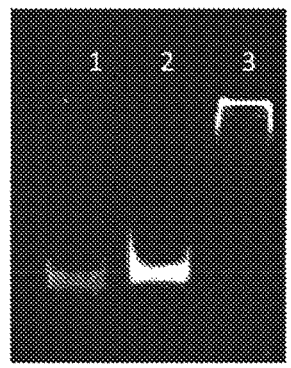
FIG. 6 is a gel electrophoresis image showing results of production of a peptide/CpG/SPG ternary complex in an Example 5.

FIG. 6 shows the result of fluorescence imaging after using SYBR Gold to stain the acrylamide gel after electrophoresis. Disappearance of the band of the OVA peptide-dA40(S) measured at lane 1 simultaneous with the CpG DNA-dA40(S) band measured at lane 2 was confirmed by the lane of reaction products after mixing (lane 3: complex (peptide/CpG/SPG)). Based on these results, both the antigenic peptide-dA40(S) and CpG DNA-dA40(S) complex were understood to have complexed with SPG, and a complex was understood to be generated that had a higher molecular weight (OVA peptide-dA40(S)/CpG DNA-dA40(S)/SPG ternary complex). In the present example, the mole ratios of SPG, OVA peptide-dA40(S) and CpG DNA-dA40(S) were adjusted such that a maximum of 7 molecular chains of dA40(S) were included per one molecule of the ternary complex. Moreover, the ternary complex is thought to have been generated because the molar ratio of OVA peptide-dA40(S) to CpG DNA-dA40(S) was 1:1, and there is thought to be no difference between these compounds in the ability to form a complex with SPG.

Ternary complexes were prepared by the aforementioned method for antigenic peptide/nucleotide conjugates having the below-listed amino acid sequences as antigenic peptides other than the OVA peptide.

TABLE 1

| Origin of Peptide | Amino Acid Sequence |
|---|---|
| ovalbumin (OVA) | SIINFEKL (SEQ ID No. 1) |
| mouse melanin-producing cell gp100 | EGSRNQDWL (SEQ ID No. 3) |
| human melanin-producing cell gp100 | KVPRNQDWL (SEQ ID No. 4) |
| CT26 (large intestine carcinoma strain) | SPSYVYHQF (SEQ ID No. 5) |
| influenza virus HA | IYSTVASSL (SEQ ID No. 6) |
| influenza virus NP | ASNENMDTM (SEQ ID No. 7) |
| influenza virus PA | SSLENFRAYV (SEQ ID No. 8) |
| β-galactosidase | DAPIYTNV (SEQ ID No. 9) |
| MuLV (mouse leukemia virus) p15E | KSPWFTTL (SEQ ID No. 10) |
| SeV (hemagglutinating virus of Japan) | FAPGNYPAL (SEQ ID No. 11) |
| MCMV (mouse cytomegalovirus) IE1 | YPHFMPTNL (SEQ ID No. 12) |
| LCMV (lymphocytic choriomeningitis virus) gp33 | KAVYNFATM (SEQ ID No. 13) |

TABLE 1-continued

| Origin of Peptide | Amino Acid Sequence |
| --- | --- |
| LCMV NP396 | FQPQNGQFI (SEQ ID No. 14) |
| LCMV NP118 | RPQASGVYM (SEQ ID No. 15) |
| malaria protozoa Pb9 | SYIPSAEKI (SEQ ID No. 16) |
| HIV P18-I10 | RGPGRAFVTI (SEQ ID No. 17) |
| BCG MPT51 | GGPHAVYLL (SEQ ID No. 18) |
| human CEA (human embryonic cell cancer antigen) | EAQNTTYL (SEQ ID No. 19) |
| P815 (mouse-derived antigen-presenting cell) | LPYLGWLVF (SEQ ID No. 20) |
| HBsAg (B-type hepatitis virus antigen) | IPQSLDSWWTSL (SEQ ID No. 21) |
| HSV-1 (mouse herpes simplex virus) gB | SSIEFARL (SEQ ID No. 22) |
| HY (male specific antigen) Uty | WMHHNMDLI (SEQ ID No. 23) |
| EGFP (enhanced green fluorescent protein) | HYLSTQSAL (SEQ ID No. 24) |
| HER2 | TYLPTNASL (SEQ ID No. 25) |
| VSV (vesicular stomatitis virus) NP | RGYVYQGL (SEQ ID No. 26) |
| polio virus MT | RRLGRTLLL (SEQ ID No. 27) |

Example 6: Evaluation of Peptide-Specific Immune Response Due to Antigenic Peptide/CpG/SPG Ternary Complex One of the following was intradermally administered once to mice (C57BL/6 mouse, male, 7 weeks old): (1) the OVA peptide-dA40(S)/SPG complex (5 µg) prepared in Example 2, (2) OVA peptide-dA40(S)/SPG complex (5 µg) and CpG DNA (30 µg), (3) OVA peptide-dA40(S)/SPG complex (5 µg) and CpG DNA-dA40(S)/SPG complex (30 µg, prepared in the same manner as in Example 5, except for the use of a 10% DMSO aqueous solution of OVA peptide-dA40A(S)), and (4) the OVA peptide-dA40(S)/CpG DNA-dA40(S)/SPG ternary complex (5 µg) prepared in Example 5. An investigation was performed to see whether antigen-specific interferon-γ (IFN-γ) was induced by, one week after administration, harvesting spleen cells from the mice, placing the cells in 96 wells ($1.0 \times 10^6$ cells/well), and then stimulating the cells using OVA peptide (10 µg/mL).

Figure 7:
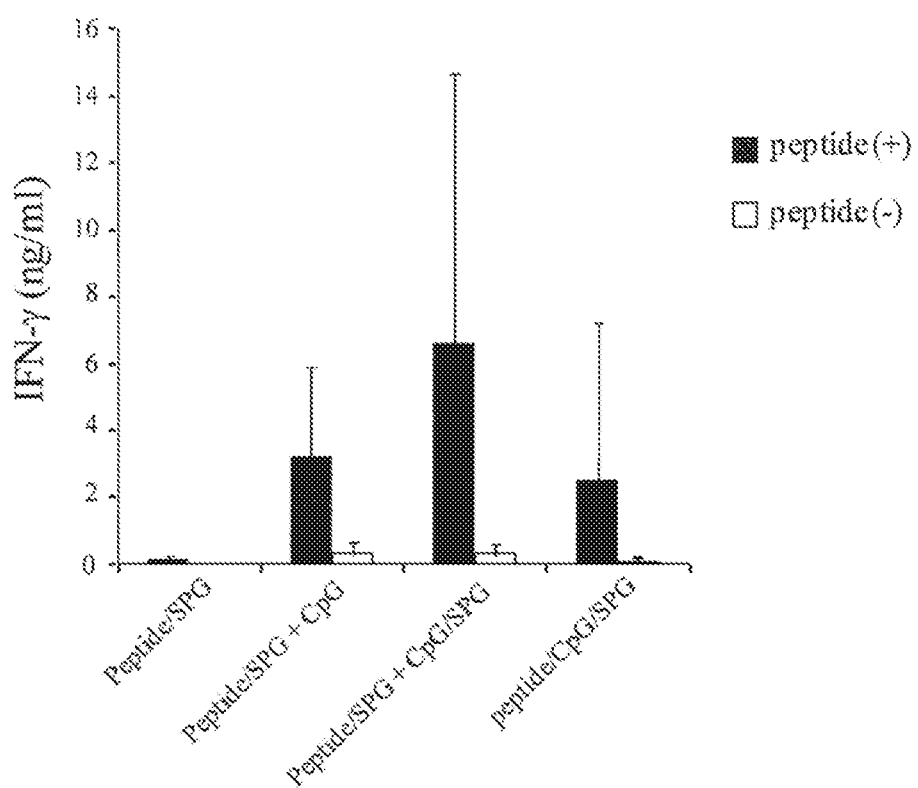
FIG. 7 is a graph showing determination of an amount of produced antigenic peptide-specific IFN-γ produced by using an antigenic peptide to stimulate spleen cells of mice, in which immunity is induced by various samples in an Example 6.

Then 24 hours after stimulating the spleen cells by OVA peptide, enzyme-linked immunosorbent assay (ELISA) was used to quantitatively measure IFN-γ in the culture medium. Results are shown in FIG. 7. As shown in Example 3, although an interferon response specific to OVA peptide could not be induced by OVA peptide-dA40(S)/SPG complex alone, a strong interferon response was induced when OVA peptide-dA40(S)/SPG complex and CpG DNA were simultaneously administered. Furthermore, the case of administration of OVA peptide-dA40(S)/SPG complex and CpG DNA simultaneously was confirmed to induce about the same degree of interferon as that of administration of the OVA peptide-dA40(S)/CpG DNA-dA40(S)/SPG ternary complex. Quite interestingly, the induction of a strong interferon response was confirmed in the case of simultaneous administration of OVA peptide-dA40(S)/SPG complex and CpG DNA-dA40(S)/SPG complex. Based on these results, the effects of take-up of OVA peptide by antigen-presenting cells and stimulation of cells through TLR9 by CpG DNA were understood to each be realized more due to administration of OVA peptide-dA40(S)/CpG DNA-dA40(S)/SPG ternary complex.

Example 7: Evaluation of Inducibility of Peptide-Specific Cytolytic T-Lymphocytes by Antigenic Peptide/CpG/SPG Ternary Complex The (1) OVA peptide, (2) OVA peptide and CpG DNA, (3) OVA peptide and CpG DNA-dA40(S)/SPG complex, or (4) OVA peptide-dA40(S)/CpG DNA-dA40(S)/SPG ternary complex prepared in Example 5 of Example 6 was intradermally administered, mouse spleen cells were harvested and stimulated using OVA peptide-dA40(S)/SPG complex, and the stimulated cells were cultured for 6 days. Then after antibody staining, a flow cytometer was used to evaluate the fraction of T cells that had cytotoxic specificity (CD8 positive) for OVA peptide.

Figure 8:
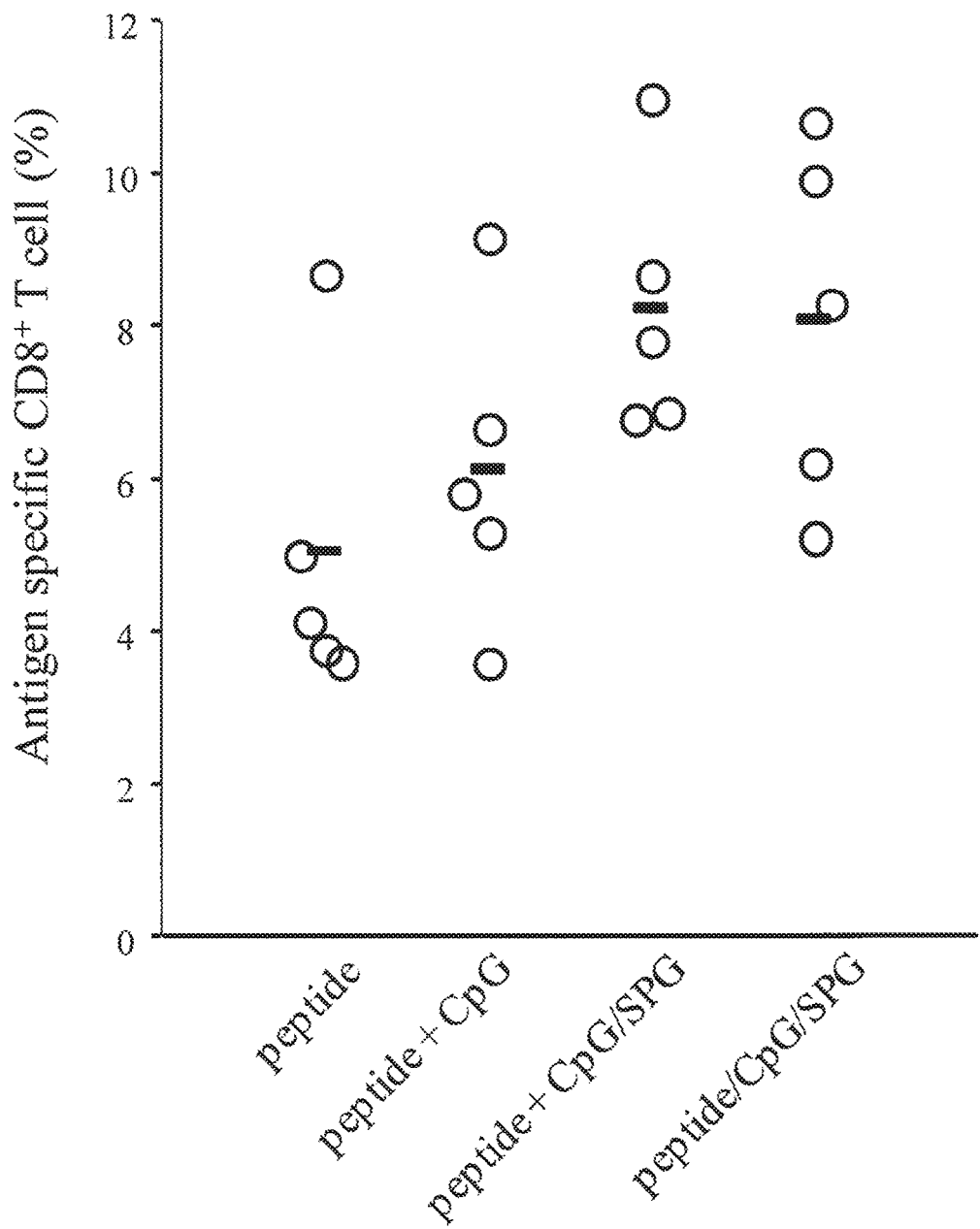
FIG. 8 is a graph showing a fraction of antigenic peptide-specific cytolytic T-lymphocytes, grown by using an antigenic peptide to stimulate spleen cells of mice, in which immunity is induced by various samples in an Example 7.

The fraction of CD8-positive T cells specific for OVA peptide among the CD8-positive T cells is shown in FIG. 8. In comparison to the case (peptide) of administration of OVA peptide alone and the case (peptide+CpG) of simultaneous administration of OVA peptide and CpG DNA, the fraction of OVA peptide-specific CD8-positive T cells could be increased in the case (peptide+CpG/SPG) in which OVA-peptide-dA40(S)/SPG complex and CpG DNA-dA40(S)/SPG complex were administered or the case (peptide/CpG/SPG) in which OVA peptide-dA40(S)/CpG DNA-dA40(S)/SPG ternary complex was administered.

Example 8: Immune Response to Melanoma Cell-Specific Antigen Protein-Derived Peptide (Evaluation of Peptide-Specific Immune Response Due to Antigenic Peptide/CpG/SPG Ternary Complex)

One of the following was intradermally administered once to mice (C57BL/6 mouse, male, 7 weeks old): (1) CpG DNA-dA40(S)/SPG complex (30 µg) and gp100 peptidedA40(S)/SPG complex (5 μg) prepared in the same manner as in Examples 1 and 2, by using an antigenic peptide (gp100) having an amino acid sequence (EGSRNQDWL, SEQ ID No. 3) derived from mouse melanoma cell-specific antigen protein; and (2) gp100 peptide-dA40(S)/CpG DNA-dA40(S)/SPG ternary complex (5 μg). An investigation was performed to see whether antigen-specific interferon-γ (IFN-γ) was induced by, one week after administration, harvesting spleen cells from the mice, placing the cells in 96 wells ($1.0 \times 10^6$ cells/well), and then stimulating the cells using gp100 peptide (10 μg/mL).

Figure 9:
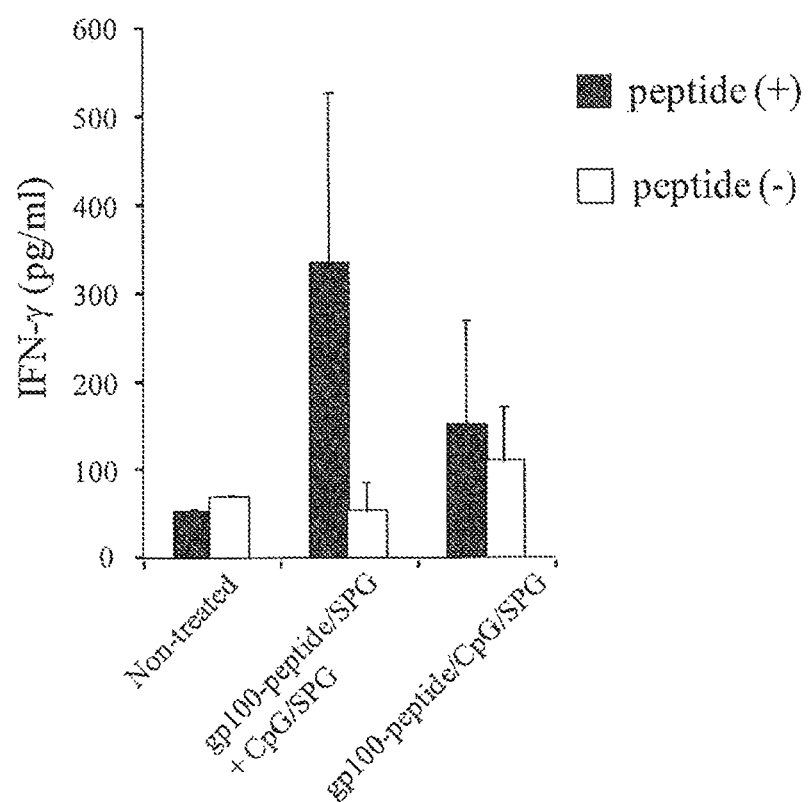
FIG. 9 is a graph showing determination of an amount of produced antigenic peptide-specific IFN-γ produced by using an antigenic peptide to stimulate spleen cells of mice, in which immunity is induced by various samples in an Example 8.

Then 24 hours after stimulating the spleen cells by gp100 peptide, enzyme-linked immunosorbent assay (ELISA) was used to quantitatively measure IFN-γ in the culture medium. Results are shown in FIG. 9. As shown in Example 3, a gp100 peptide-specific interferon response could not be induced by gp100 peptide-dA40(S)/SPG complex alone (data not shown). However, a strong interferon reaction was induced when gp100 peptide-dA40(S)/SPG complex and CpG DNA-dA40(S)/SPG complex were simultaneously administered. Furthermore, interferon induction was similarly confirmed also by administration of gp100 peptide-dA40(S)/CpG DNA-dA40(S)/SPG ternary complex. Based on these results, a peptide-specific immune response was understood to have been induced also by administration to mice of an antigenic peptide/CpG/SPG ternary complex that included an antigenic peptide other than OVA peptide.

Example 9: Immune Response Using Different Antigenic Peptides

Using the method described in Example 5 and antigenic peptides other than OVA peptide, antigenic peptide-dA40(S)/CpG DNA-dA40(S)/SPG ternary complexes were prepared, and then peptide-specific immune responses were evaluated by the procedure described in Example 6. The amino acid sequences of the utilized antigenic peptides and experimental results (presence/absence of induction of antigenic peptide-specific IFN-γ) are shown below in Table 2. Furthermore, the amino acid sequence (SEQ ID No. 28) shown for the no. 2 entry is a random sequence of the OVA peptide (no. 1). Although antigenic peptide including ternary complex was used to stimulate spleen cells placed in wells after harvesting from mice for case nos. 1, 3 and 4 in Table 2, for entry no. 2, OVA peptide was used that had the same amino acid composition, although having a different amino acid sequence. Moreover, among the examples of IFN response in Table 2, "+" indicates that production of IFN-γ was observed, and "−" indicates that production of IFN-γ was not observed. An antigenic peptide-specific IFN response was observed in the cases (nos. 1, 3, 4 and 5) in which spleen cells were simulated by peptide having an amino acid sequence that was identical to the antigenic peptide used in the ternary complex administered to mice. In contrast, no IFN production whatsoever was observed in the case (no. 2) of stimulation of spleen cells by the peptide having a different amino acid sequence. Based on these results, the peptide-specific immune response is understood to have been induced by the ternary complex administered to the mice.

TABLE 2

| No. | Peptide Sequence | IFN Response |
|---|---|---|
| 1 | SIINFEKL (SEQ ID No. 1) | + |
| 2 | FKILSENI (SEQ ID No. 28) | − |
| 3 | EGSRNQDWL (SEQ ID No. 3) | + |
| 4 | KVPRNQDWL (SEQ ID No. 4) | + |
| 5 | SPSYVYHQF (SEQ ID No. 5) | + |

Example 10: (1) Preparation of Peptide/β-1,3-Glucan Complex by Introduction of Antigenic Peptide to Glucose Residue on SPG Main Chain or Side Chain Introduction of antigenic peptide to a glucose residue on the main chain or side chain of SPG utilizing the "quick reaction" (Husigen reaction) between an alkyne and azide compound was investigated. The reaction scheme is indicated below. Carbonyldiimidazole (CDI) and propargylamine (PA) were reacted with the primary alcohol present at the 6 position of the glucose residue of the SPG, and through the generated carbamate bond, the alkyne was introduced in a site-specific manner to the main chain or side chain glucose residue of the SPG (SPG-PA). Since the ratio of the number of alkyne residues introduced to SPG to the number of glucose residues was 10 to 20%, the major portion of alkyne residues are thought to have been introduced to the glucose residue on the side chain due to steric hindrance in the vicinity of the glucose residue of the main chain. In the presence of copper catalyst, the SPG derivatives obtained in this manner were reacted with antigenic peptides (peptide (N3): obtained from Gene Science Inc., used as the azide-decorated OVA peptide in the present example) decorated by the azide group at the C terminus to prepare peptide/β-1,3-glucan complexes by the "quick reaction".

[Formula 3]

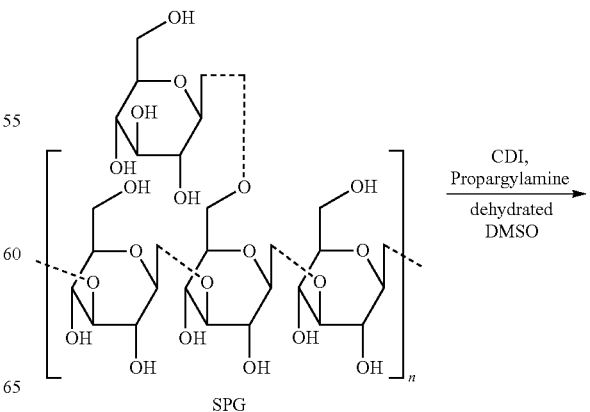

SPG

CDI, Propargylamine
dehydrated DMSO

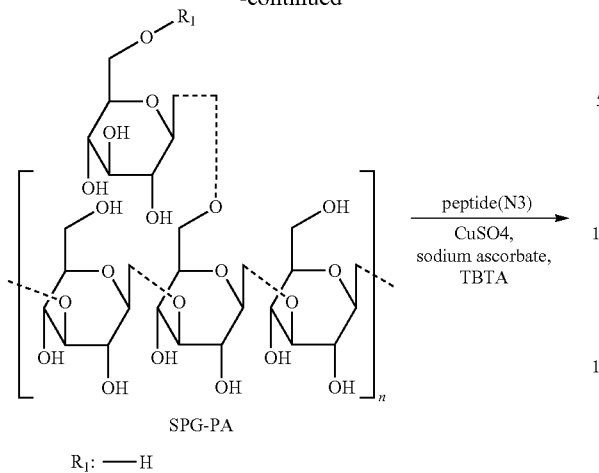

SPG-PA

R₁: —H

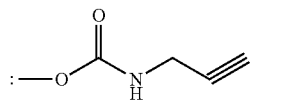

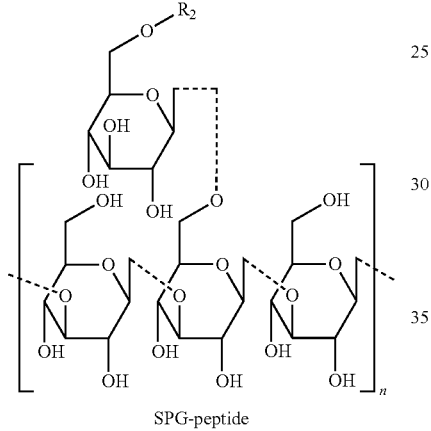

SPG-peptide

R₂: —H

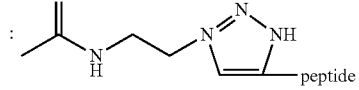

[Formula 4]

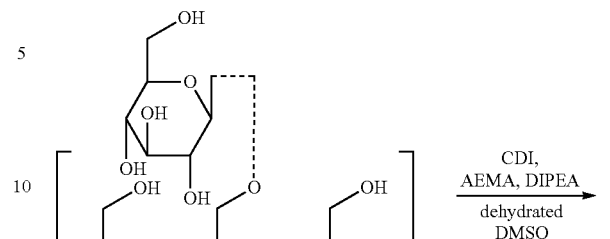

SPG

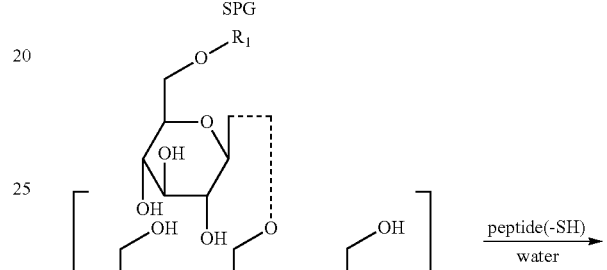

SPG-AEMA

R₁: —H

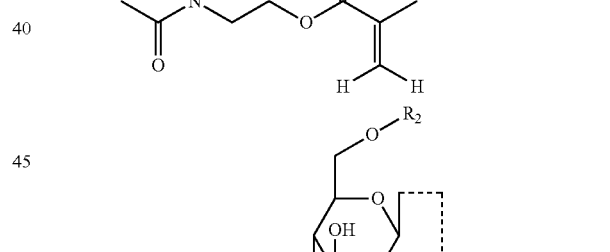

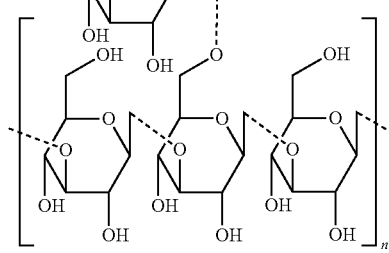

R₂: —H

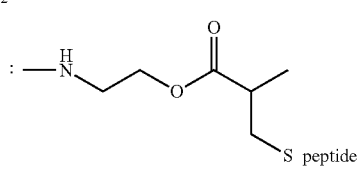

Example 11: (2) Preparation of Peptide/β-1,3-Glucan Complex by Introduction Through Covalent Bond of Antigenic Peptide to Glucose Residue on SPG Main Chain or Side Chain Introduction of antigenic peptide to a glucose residue on the main chain or side chain of SPG was investigated using the Michael addition reaction between an α,β-unsaturated ketone and a thiol. The reaction scheme is indicated below. In the presence of N,N-diisopropylethylamine (DIPEA), carbonyldiimidazole (CDI) and 2-aminoethylmethaciylate (AEMA) were reacted with the primary alcohol present at the 6 position of the glucose residue of the SPG side chain, and a methaciyloyl group was introduced through the generated carbamate bond (SPG-AEMA). Thereafter, in the presence of tris(2-carboxyethyl)phosphine (TCEP), the antigenic peptide (peptide(—SH): obtained from Gene Science Inc.) having cysteine introduced to the C terminus was reacted with SPG-AEMA to prepare the peptide/β-1,3-glucan complex.

Example 12: Evaluation of Antigenic
Peptide-Specific Immune Response Due to
Antigenic Peptide/CpG/SPG Ternary Complex in
which Antigenic Peptide is Covalently Bonded to
Glucose Residue of Side Chain of Polysaccharide
Having the β-1,3-Glucan Backbone Using the same methods as those mentioned in Examples 2 and 5, the peptide/β-1,3-glucan complexes prepared in Examples 10 and 11 were complexed with CpG DNA-dA40 (S) to prepare antigenic peptide/CpG/SPG ternary complexes. These complexes were intradermally administered once (amount equivalent to 30 μg CpG DNA) to C57BL/6 mice (male, 7 weeks old). An investigation was performed to see whether antigen-specific interferon-γ (IFN-γ) was induced by, one week after administration, harvesting spleen cells from the mice, placing the cells in 96 wells ($1.0 \times 10^6$ cells/well), and then stimulating the cells using OVA peptide (10 μg/mL). The utilized antigenic peptide amino acid sequences and experimental results (presence or absence of induction of antigenic peptide-specific IFN-γ) are shown below in Table 3. Furthermore, in the same manner as in Example 9, the amino acid sequence (SEQ ID No. 28) indicated in case no. 2 was a random sequence of the OVA peptide (case no. 1). In case nos. 1, 3 and 4 of Table 3, antigenic peptide included in the ternary complex was used for stimulation of the spleen cells placed in the wells after harvesting from the mice. However, for case no. 2, although the amino acid composition was the same as that of OVA peptide, the amino acid sequence of the utilized antigenic peptide was different from that of OVA peptide. Moreover, in the "IFN Response" column of Table 3, "+" indicates that production of IFN-γ was observed, and "−" indicates that production of IFN-γ was not observed. Similarly to the results of Example 9, in the cases (nos. 1, 3 and 4) of stimulation of spleen cells by peptides having the same amino acid sequence as that of the antigenic peptide used in the ternary complex administered to the mice, antigenic peptide-specific IFN responses were observed, and in contrast, IFN production was not observed whatsoever in the case (no. 2) of stimulation of the spleen cells by the peptide having a different amino acid sequence. Based on these results, induction of a peptide-specific immune response is understood to have occurred due to the ternary complex administered to the mice.

TABLE 3

| No. | Peptide Sequence | IFN Response |
|---|---|---|
| 1 | SIINFEKL (SEQ ID No. 1) | + |
| 2 | FKILSENI (SEQ ID No. 28) | − |
| 3 | EGSRNQDWL (SEQ ID No. 3) | + |
| 4 | SPSYVYHQF (SEQ ID No. 5) | + |

Furthermore, the present disclosure can be embodied in various ways and can undergo various modifications without departing from the broad spirit and scope of the disclosure. Moreover, the embodiments described above are for explaining the present disclosure, and do not limit the scope of the present disclosure. In other words, the scope of the present disclosure is as set forth in the Claims and not the embodiments. Various changes and modifications that are within the scope disclosed in the claims or that are within a scope that is equivalent to the claims of the disclosure are also included within the scope of the present disclosure.

This application claims the benefit of Japanese Patent Application No. 2014-21333, filed on Feb. 6, 2014, including the Specification, Claims, Figures and Abstract of Japanese Patent Application No. 2014-21333. The entire disclosure of Japanese Patent Application No. 2014-21333 is incorporated by reference herein.

The invention claimed is:

1. A peptide/β-1,3-glucan complex, comprising:
   a polysaccharide having a β-1,3-glucan backbone; and
   a peptide/polynucleotide conjugate in which an antigenic peptide is bonded covalently to a polynucleotide or derivative thereof, wherein
   the polynucleotide or derivative thereof of the peptide/polynucleotide bonds through hydrogen bonding with the polysaccharide having the β-1,3-glucan backbone, and forms a complex having a triple helix structure consisting of one molecular chain of the polynucleotide or derivative thereof and two molecular chains of the polysaccharide having the β-1,3-glucan backbone.

2. The peptide/β-1,3-glucan complex according to claim 1, wherein the polysaccharide having the β-1,3-glucan backbone is schizophyllan, lentinan, scleroglucan or curdlan.

3. The peptide/β-1,3-glucan complex according to claim 1, wherein the polynucleotide or derivative thereof is polydeoxyadenosine.

4. The peptide/β-1,3-glucan complex according to claim 1, wherein
   the polynucleotide or derivative thereof is a polynucleotide derivative in which at least a portion of phosphodiester bonds of DNA or RNA is substituted with a phosphorothioate group.

5. The peptide/β-1,3-glucan complex according to claim 4, wherein
   in the polynucleotide derivative in which the at least the portion of phosphodiester bonds of DNA or RNA is substituted with a phosphorothioate group, at least 50% of the phosphodiester bonds are substituted with the phosphorothioate group.

6. The peptide/β-1,3-glucan complex according to claim 1, wherein
   the polynucleotide or derivative thereof and the antigenic peptide included in the peptide/polynucleotide conjugate are bonded through covalent bonding formed by:
   a cycloaddition reaction between an alkyne and an azide derivative,
   a reaction between a maleimide group and a thiol group, or
   a reaction between a thiol group of a thiol-modified nucleic acid and a thiol group of a peptide C-terminal cysteine residue.

7. The peptide/β-1,3-glucan complex according to claim 6, wherein the polysaccharide having the β-1,3-glucan backbone is schizophyllan, lentinan, scleroglucan or curdlan.

8. The peptide/β-1,3-glucan complex according to claim 1, wherein
   the peptide/β-1,3-glucan complex further comprises a polynucleotide or derivative thereof having a partial base sequence having immunostimulatory activity;

the polynucleotide or derivative thereof and the polysaccharide having the β-1,3-glucan backbone are bonded by hydrogen bonding to form a complex having a triple helix structure consisting of one molecular chain of the polynucleotide or derivative thereof and two molecular chains of the polysaccharide having the β-1,3-glucan backbone.

9. The peptide/β-1,3-glucan complex according to claim 8, wherein a portion of the polynucleotide or derivative thereof forming the complex having the triple helix structure is poly-deoxyadenosine.

10. The peptide/β-1,3-glucan complex according to claim 8, wherein the portion of the polynucleotide or derivative thereof forming the complex having the triple helix structure is a polynucleotide derivative in which at least a portion of phosphodiester bonds of DNA or RNA is substituted with a phosphorothioate group.

11. The peptide/β-1,3-glucan complex according to claim 10, wherein
in the polynucleotide derivative in which the portion of phosphodiester bonds of DNA or RNA is substituted with a phosphorothioate group, at least 50% of the phosphodiester bonds are substituted with the phosphorothioate group.

12. A pharmaceutical composition comprising:
a polynucleotide or derivative thereof having a partial base sequence having immunostimulatory activity, and
the peptide/β-1,3-glucan complex of claim 1.

13. The pharmaceutical composition according to claim 12, wherein
the polynucleotide or derivative thereof and the polysaccharide having the β-1,3-glucan backbone are bonded by hydrogen bonding to form a complex having a triple helix structure consisting of one molecular chain of the polynucleotide or derivative thereof and two molecular chains of the polysaccharide having the β-1,3-glucan backbone.

14. The pharmaceutical composition according to claim 13, wherein
the polysaccharide having the β-1,3-glucan backbone included in the polynucleotide/β-1,3-glucan complex having a triple helix structure is schizophyllan, lentinan, scleroglucan, or curdlan.

15. A pharmaceutical composition comprising the peptide/β-1,3-glucan complex according to claim 8.

16. The peptide/β-1,3-glucan complex according to claim 6, wherein the polysaccharide having the β-1,3-glucan backbone is schizophyllan, lentinan, scleroglucan or curdlan.

* * * * *